United States Patent
Brinkman et al.

(10) Patent No.: US 12,161,643 B2
(45) Date of Patent: Dec. 10, 2024

(54) STABLE FORMULATIONS OF SHR0302

(71) Applicant: ARCUTIS BIOTHERAPEUTICS, INC., Westlake Village, CA (US)

(72) Inventors: Herbert R. Brinkman, Fort Collins, CO (US); Jason Michael Carbol, Petaluma, CA (US)

(73) Assignee: ARCUTIS BIOTHERAPEUTICS, INC., Westlake Village, CA (US)

( * ) Notice: Subject to any disclaimer, the term of this patent is extended or adjusted under 35 U.S.C. 154(b) by 0 days.

(21) Appl. No.: 18/065,772

(22) Filed: Dec. 14, 2022

(65) Prior Publication Data

US 2023/0181591 A1 Jun. 15, 2023

Related U.S. Application Data

(60) Provisional application No. 63/370,740, filed on Aug. 8, 2022, provisional application No. 63/289,780, filed on Dec. 15, 2021.

(51) Int. Cl.
| | | |
|---|---|---|
| *A61K 31/519* | (2006.01) | |
| *A61K 9/00* | (2006.01) | |
| *A61K 47/20* | (2006.01) | |
| *A61K 47/34* | (2017.01) | |

(52) U.S. Cl.
CPC .......... *A61K 31/519* (2013.01); *A61K 9/0014* (2013.01); *A61K 47/20* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 3,711,602 A * | 1/1973 | Herschler | A61K 9/0014 514/711 |
| 3,934,013 A | 1/1976 | Poulsen | |
| 9,422,300 B2 | 8/2016 | Sun et al. | |
| 9,527,851 B2 | 12/2016 | Zhang et al. | |
| 10,023,577 B2 | 7/2018 | Sun et al. | |
| 10,150,770 B2 | 12/2018 | Sun et al. | |
| 10,428,074 B2 | 10/2019 | Zhang et al. | |
| 10,786,507 B2 | 9/2020 | Lu et al. | |
| 11,628,177 B2 * | 4/2023 | Osborne | A61K 9/107 514/175 |
| 11,730,740 B2 * | 8/2023 | Osborne | A61P 29/00 514/265.1 |
| 2017/0044171 A1 | 2/2017 | Zhang et al. | |
| 2019/0060311 A1 | 2/2019 | Shanler | |
| 2019/0127364 A1 | 5/2019 | Kozak et al. | |
| 2020/0197397 A1 | 6/2020 | Arkin et al. | |
| 2022/0031705 A1 * | 2/2022 | Osborne | A61K 31/573 |
| 2022/0133728 A1 * | 5/2022 | Higham | A61N 5/0616 514/265.1 |
| 2022/0152033 A1 * | 5/2022 | Osborne | A61P 17/14 |
| 2023/0226083 A1 * | 7/2023 | Osborne | A61K 47/34 424/489 |
| 2023/0338383 A1 * | 10/2023 | Osborne | A61K 9/107 |
| 2023/0414511 A1 * | 12/2023 | Osborne | A61K 9/146 |

FOREIGN PATENT DOCUMENTS

| | | | |
|---|---|---|---|
| CN | 114870016 A | 8/2022 | |
| EP | 2796460 A1 | 10/2014 | |
| EP | 3714887 A1 * | 9/2020 | ........... A61K 31/519 |
| WO | 2011076209 A2 | 6/2011 | |
| WO | 2019/084383 A1 | 5/2019 | |
| WO | 2020025910 A1 | 2/2020 | |
| WO | 2020236950 A1 | 11/2020 | |
| WO | WO-2022027041 A1 * | 2/2022 | ........... A61K 31/519 |
| WO | 2022094082 A1 | 5/2022 | |

OTHER PUBLICATIONS

Kushwaha, "A Screening of Permeation Enhancers for Transdermal Delivery of Propofol", 2018, Journal of Bioequivalence & Bioavailability, 10, pp. 50-53 (Year: 2018).*

Lukic et al., "Towards Optimal pH of the Skin and Topical Formulations: From the Current State of the Art to Tailored Products", 2021, Cosmetics, 8, pp. 1-18 (Year: 2021).*

International Search Report and the Written Opinion of the International Searching Authority, issued in corresponding International Application No. PCT/US2022/081535, dated Apr. 24, 2023, 26 pages.

Lauren Hewett, "Reistone Announces Positive Results from a Phase II Study Evaluating SHR0302 Ointment for Patients with Mild-to-Moderate Atopic Dermatitis" Nov. 4, 2021, retrieved from https://nationaleczema.org/blog/reistone-101121.

Lukic Milica et al., Towards Optimal pH of the Skin and Topical Formulations: From the Current State of the Art to Tailored Products, vol. 8, No. 3, Aug. 4, 2021, p. 69, XP055951998, DOI: 10.3390/cosmetics8030069.

Heather A.E. Benson "Transdermal Drug Delivery: Penetration Enhancement Techniques" Current Drug Delivery, (2005), 2(1):23-33.

(Continued)

*Primary Examiner* — Jeffrey H Murray
*Assistant Examiner* — Madeline E Braun
(74) *Attorney, Agent, or Firm* — ROTHWELL, FIGG, ERNST & MANBECK, P.C.

(57) ABSTRACT

The disclosure relates to stable topical pharmaceutical compositions of SHR0302 (also known as ARQ-250). In certain embodiments, pharmaceutical compositions of SHR0302 having a pH of less than about 4.6 have improved stability and do not exhibit crystal formation of the API. In certain embodiments, pharmaceutical compositions of SHR0302 comprising about 20% to about 30% dimethyl sulfoxide (DMSO) have improved stability and do not exhibit crystal formation of the API. The improved formulations of SHR0302 can exhibit acceptable commercial product shelf life and do not exhibit loss of potency of the API after prolonged storage.

14 Claims, 8 Drawing Sheets

(56) References Cited

OTHER PUBLICATIONS

Rong-Kun Chang et al. "Generic Development of Topical Dermatologic Products: Formulation Development, Process Development, and Testing of Topical Dermatologic Products" AAPS Journal, (2012), 15(1):41-52.
David W. Osborne et al. "Skin Penetration Enhancers Cited in the Technical Literature" Pharmaceutical Technology (1997), 21:58-66.
Wu-Wei Shen et al. "Effect of nonionic surfactants on percutaneous absorption of salicylic acid and sodium salicylate in the presence of dimethyl sulfoxide" J. Pharm. Sci., (1976), 65(12):1780-1783.
Bruce J. Aungst et al. "Enhancement of naloxone penetration through human skin in vitro using fatty acids, fatty alcohols, surfactants, sulfoxides and amides" International Journal of Pharmaceutics, (1986), 33(1-3):225-234.
Notice of Allowance mailed May 8, 2024 in corresponding U.S. Appl. No. 18/216,089, First Named Inventor: David W. Osborne (14 pages).

* cited by examiner

STABLE FORMULATIONS OF SHR0302

CROSS REFERENCE TO RELATED APPLICATIONS

This application claims priority to U.S. Provisional Application Ser. No. 63/289,780, filed Dec. 15, 2021, and U.S. Provisional Application Ser. No. 63/370,740, filed Aug. 8, 2022. The contents of these applications are incorporated in their entirety herein by reference.

FIELD OF THE INVENTION

The subject matter disclosed herein generally relates to stable topical formulations comprising SHR0302. In certain embodiments, the disclosure addresses the surprising discovery that formulations of SHR0302 having a pH of less than 4.6 have improved stability and do not exhibit crystal formation of the active ingredient. Additionally, in certain embodiments, the disclosure addresses the surprising discovery that formulations comprising a certain percentage of dimethyl sulfoxide have improved stability and do not exhibit crystal formation of the active ingredient.

BACKGROUND OF THE INVENTION

The present invention relates to topical pharmaceutical compositions of the JAK1 inhibitor, (3aR,5S,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2 (1H)-carboxamide, which is also known as SHR0302 or ARQ-250. SHR0302 is a potent small molecule inhibitor of JAK1 that has been shown to have a high selectively for JAK1 over JAK2, and thus has the potential to treat inflammatory diseases without causing the hematopoietic adverse effects, such as anemia, thrombocytopenia, and neutropenia, associated with JAK2 inhibition. SHR0302 is disclosed in U.S. Pat. No. 9,527,851, which is hereby incorporated by reference.

Topical application of potent pharmacological agents for treating skin diseases can provide superior delivery, lower systemic exposure, and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (APIs) for application to the skin. To assure consistent delivery of the API into or across the skin, it must remain either: (1) dissolved over the shelf life of the topical product, or (2) suspended as particles having unchanged crystal habit and unchanged particle size distribution over the shelf life of the topical product.

Generally, the most consistent skin permeation of a drug from a topical product occurs when the active ingredient is dissolved in the formulation. For this reason, formulators generally avoid developing a topical product that will have particles or crystals of the active ingredient precipitate during storage according to labeled storage instructions. Precipitation of the active ingredient can occur for various reasons. Particular active ingredients, when formulated with particular pharmaceutical excipients will tend to form supersaturated solutions. At the time of manufacture, all of the active ingredient will be in solution. After days, weeks, or months, this metastable topical product will equilibrate and active ingredient particles will form. Regardless of the reason, irreversible precipitation of the active ingredient during storage of a topical product can have profound effects on the bioavailability and efficacy of a topical product, since only dissolved active ingredients can penetrate into intact stratum corneum, the outermost layer of epithelium of the skin.

SUMMARY OF THE INVENTION

The present invention relates to improved topical formulations comprising SHR0302. The inventors of the present invention have produced stable pharmaceutical compositions of SHR0302 that exhibit decreased susceptibility to crystallization of the active pharmaceutical ingredient ("API"). The pharmaceutical compositions of the present invention can be stable at controlled room temperature for 6, 12, or 18 months. In certain embodiments, the inventors of the present invention have made the surprising discovery that formulations of SHR0302 (also known as ARQ-250) having a pH of less than about 4.6 have improved stability and do not exhibit crystal formation of the API. Alternatively, in certain embodiments, the inventors of the present invention have made the surprising discovery that formulations of SHR0302 having about 20% to about 30% of dimethyl sulfoxide have improved stability and do not exhibit crystal formation of the API. The improved formulations of SHR0302 address the aforementioned issues, exhibit acceptable commercial product shelf life, and do not exhibit loss of potency of the API after prolonged storage.

In certain embodiments of the present invention, a topical pharmaceutical composition is provided. The topical pharmaceutical composition comprises a pharmaceutically effective amount of SHR0302, wherein the pharmaceutical composition has a pH of less than 4.6. In certain embodiments, the pharmaceutical composition has a pH between about 3.8 and about 4.6. In certain embodiments, the pharmaceutical composition has a pH between about 3.8 and about 4.2.

In certain embodiments, the topical pharmaceutical composition comprises SHR0302 in an amount of about 0.1 to about 1.0% w/w. In certain embodiments, the topical pharmaceutical composition further comprises laureth-4. In certain embodiments, the topical pharmaceutical composition comprises laureth-4 in an amount of about 0.5 to about 5% w/w.

In certain embodiments, the topical pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment.

In certain embodiments, the topical pharmaceutical composition is stable at controlled room temperature for at least 6 months, 7 months, 8 months, 12 months, or 18 months.

In another embodiment, a topical pharmaceutical composition comprising a pharmaceutically effective amount of SHR0302 and laureth-4 is provided. The pharmaceutical composition has a pH of less than 4.6. In certain embodiments, the pharmaceutical compositions has a pH between about 3.8 and about 4.6. In certain embodiments, the pharmaceutical composition has a pH between about 3.8 and about 4.2.

In certain embodiments, the topical pharmaceutical composition comprises SHR0302 in an amount of about 0.1 to about 1.0% w/w. In certain embodiments, the topical pharmaceutical composition further comprises laureth-4. In certain embodiments, the topical pharmaceutical composition comprises laureth-4 in an amount of about 0.5 to about 5% w/w.

In certain embodiments, the topical pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment.

In certain embodiments, the topical pharmaceutical composition is stable at controlled room temperature for at least 6 months, 7 months, 8 months, 12 months, or 18 months.

In another embodiment, a topical pharmaceutical composition comprising a pharmaceutically effective amount of SHR0302 is provided. The topical pharmaceutical composition further comprises one or more of dimethyl sulfoxide, laureth-4, butylated hydroxytoluene, benzyl alcohol, propylene glycol, polyethylene glycol 200, cyclomethicone, dimethicone, ST-Elastomer 10, Pemulen TR 1, Carbopol 974P, and a pH adjusting agent. The topical pharmaceutical composition has a pH of less than 4.6. In certain embodiments, the pharmaceutical composition has a pH between about 3.8 and about 4.6. In certain embodiments, the pharmaceutical composition has a pH between about 3.8 and about 4.2. In certain embodiments, the topical pharmaceutical composition is a cream.

In certain embodiments, the pharmaceutical composition comprises an amount of about 0.1 to about 1.0% w/w of SHR0302. In certain embodiments, the pharmaceutical composition comprises an amount of about 20% to about 40% w/w of dimethyl sulfoxide. In certain embodiments, the pharmaceutical composition comprises an amount of about 0.5% to about 5% w/w of laureth-4. In certain embodiments, the pharmaceutical composition comprises an amount of about 0.01% to about 5% w/w of butylated hydroxytoluene. In certain embodiments, the pharmaceutical composition comprises an amount of about 0.5% to about 5% w/w of benzyl alcohol. In certain embodiments, the pharmaceutical composition comprises an amount of about 5% to about 20% w/w of propylene glycol. In certain embodiments, the pharmaceutical composition comprises an amount of about 5% to about 20% w/w of polyethylene glycol 200. In certain embodiments, the pharmaceutical composition comprises an amount of about 5% to about 10% w/w of cyclomethicone. In certain embodiments, the pharmaceutical composition comprises an amount of about 0.5% to about 5% w/w of dimethicone. In certain embodiments, the pharmaceutical composition comprises an amount of about 0.5% to about 5% w/w of ST-Elastomer 10. In certain embodiments, the pharmaceutical composition comprises an amount of about 0.1 to about 1.0% w/w of Pemulen TR 1. In certain embodiments, the pharmaceutical composition comprises an amount of about 0.1 to about 1.5% w/w of Carbopol 974P.

In certain embodiments, the topical pharmaceutical composition is stable at controlled room temperature for at least 6 months, 7 months, 8 months, 12 months, or 18 months.

In another embodiment, a topical pharmaceutical composition comprising a pharmaceutically effective amount of SHR0302 is provided. The topical pharmaceutical composition further comprises one or more of N-methyl-2 pyrrolidone, laureth-4, butylated hydroxytoluene, methylparaben, propylparaben, Crodafos CES, isopropyl palmitate, white petrolatum, propylene glycol, polyethylene glycol 200, a pH adjusting agent, and xanthan gum. The topical pharmaceutical composition has a pH of less than 4.6. In certain embodiments, the pharmaceutical compositions has a pH between about 3.8 and about 4.6. In certain embodiments, the pharmaceutical composition has a pH between about 3.8 and about 4.2. In certain embodiments, the topical pharmaceutical composition is a cream.

In certain embodiments, the pharmaceutical composition comprises an amount of about 0.1 to about 1.0% w/w of SHR0302. In certain embodiments, the pharmaceutical composition comprises an amount of about 15% to about 40% w/w of N-methyl-2 pyrrolidone. In certain embodiments, the pharmaceutical composition comprises an amount of about 0.5% to about 5% w/w of laureth-4. In certain embodiments, the pharmaceutical composition comprises an amount of about 0.01% to about 5% w/w of butylated hydroxytoluene. In certain embodiments, the pharmaceutical composition comprises an amount of about 0.01% to about 5% w/w of methylparaben. In certain embodiments, the pharmaceutical composition comprises an amount of about 0.01% to about 5% w/w of propylparaben. In certain embodiments, the pharmaceutical composition comprises an amount of about 5% to about 20% w/w of Crodafos CES. In certain embodiments, the pharmaceutical composition comprises an amount of about 1% to about 10% w/w of isopropyl palmitate. In certain embodiments, the pharmaceutical composition comprises an amount of about 1% to about 10% w/w of white petrolatum. In certain embodiments, the pharmaceutical composition comprises an amount of about 5% to 20% w/w of propylene glycol. In certain embodiments, the pharmaceutical composition comprises an amount of about 5% to 20% w/w of polyethylene glycol 200.

In certain embodiments, the topical pharmaceutical composition is stable at controlled room temperature for at least 6 months, 7 months, 8 months, 12 months, or 18 months.

In certain embodiments, the topical pharmaceutical composition comprises a pharmaceutically effective amount of SHR0302 and about 20% to about 30% of dimethyl sulfoxide. In certain embodiments, the pharmaceutical composition can comprise about 25% of dimethyl sulfoxide. In certain embodiments, the pharmaceutical composition comprises an amount of about 0.1% to about 1.0% w/w of SHR0302. In certain embodiments, the pharmaceutical composition comprises laureth-4, which can be present in an amount of about 0.5 to about 5% w/w. In certain embodiments, the topical pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment. In certain embodiments, the topical pharmaceutical composition is stable at controlled room temperature for at least 6 months, 7 months, 8 months, 12 months, or 18 months.

In certain embodiments, the topical pharmaceutical composition comprises a pharmaceutically effective amount of SHR0302, about 20% to about 27% of dimethyl sulfoxide, and about 0.5% to about 5% laureth-4. In certain embodiments, the pharmaceutical composition can comprise about 25% of dimethyl sulfoxide. In certain embodiments, the pharmaceutical composition comprises an amount of about 0.1% to about 1.0% w/w of SHR0302. In certain embodiments, the topical pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment. In certain embodiments, the topical pharmaceutical composition is stable at controlled room temperature for at least 6 months, 7 months, 8 months, 12 months, or 18 months.

In certain embodiments, the topical pharmaceutical composition comprises a pharmaceutically effective amount of SHR0302 that is stable at controlled room temperature for 12 months. In certain embodiments, the pharmaceutical composition comprises about 20% to about 27% of dimethyl sulfoxide. In certain embodiments, the pharmaceutical composition further comprises laureth-4 in an amount of about 0.5% to about 5% laureth-4. In certain embodiments, the pharmaceutical composition comprises an amount of about 0.1% to about 1.0% w/w of SHR0302. In certain embodiments, the topical pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

DETAILED DESCRIPTION OF THE INVENTION

Figure 1:
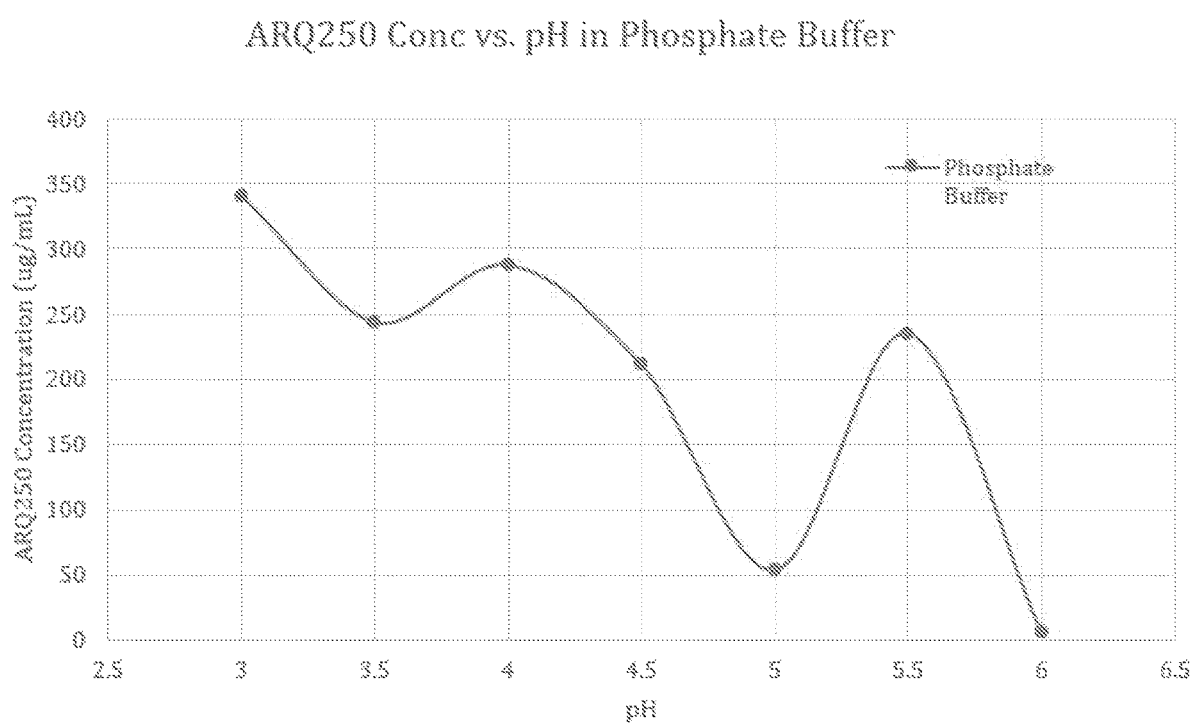
FIG. 1 illustrates a plot of SHR0302 (also known as ARQ-250) concentration in μg/mL in water as a function of pH in a phosphate buffer system. The results illustrate that SHR0302 solubility in water decreases as pH levels increase.

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients, "solvent" refers to a single solvent and two or more different solvents or a complex mixture of solvents, and "sulfate salt" includes a single sulfate salt as well as two or more different sulfate salts.

The term "about" when used in connection with a numerical value is meant to encompass numerical values within a range having a lower limit that is 5% smaller than the indicated numerical value and having an upper limit that is 5% larger than the indicated numerical value.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

A "pharmaceutically effective amount" or "therapeutically effective amount" is an amount of a pharmaceutical or therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

The term "SHR0302" or "ARQ-250" refers to (3aR,5S,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide and its salts. For example, SHR0302 includes the bisulfate salt of SHR0302, which is disclosed in U.S. Pat. No. 9,422,300 and which is incorporated by reference herein.

As used herein, the terms "subject" or "patient" most preferably refer to a human being. The terms "subject" or "patient" may include any mammal that may benefit from the compounds described herein.

The term "topical" with respect to administration of a drug or composition refers to the application of such drug or composition to the epithelial surface outside the body, including the skin or cornea. For this application, application to the inside of a body opening such as the mouth, nose or ear is not considered a topical application.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The abbreviation "w/w" represents the relative concentration of the components in the composition as "weight to weight" (i.e., percentage refers to percentage of total weight), rather than based on volume or other quantities.

The present invention relates to improved topical formulations comprising SHR0302. The inventors of the present invention have developed stable topical formulations comprising SHR0302 that can exhibit acceptable commercial product shelf life, and do not exhibit loss of potency of the API after prolonged storage.

In certain embodiments, the inventors of the present invention have discovered that topical pharmaceutical compositions of SHR0302 having a pH value equal to or greater than about 4.6 may have an increased susceptibility to crystallization of the API. In certain embodiments, the inventors of the present invention have made the surprising discovery that formulations of SHR0302 having a pH of less than about 4.6 have improved stability and do no exhibit crystal formation of the API.

In certain embodiments, the inventors of the present invention have discovered that topical pharmaceutical compositions of SHR0302 comprising less than about 30% of dimethyl sulfoxide have improved stability and do not exhibit crystal formation of the API. In certain embodiments, the topical pharmaceutical composition of SHR0302 can comprise about 20% to about 27% of dimethyl sulfoxide. In certain embodiments, the topical pharmaceutical composition of SHR0302 can comprise about 25% of dimethyl sulfoxide.

Janus kinase inhibitors (JAK inhibitors) are a class of compounds that function by inhibiting the activity of one or more enzymes in the JAK family (e.g., JAK1, JAK2, JAK3, or Tyk2). These compounds are thought to work by interfering with the JAK-STAT signaling pathway, which plays a central role in immune system function. Many inflammatory cytokines and other signaling molecules rely on the JAK pathway, and specifically JAK1. It has previously been shown that inhibition of JAK1 has been shown to treat a range of inflammatory diseases, including rheumatoid arthritis, psoriasis, Crohn's disease, and eczema. There is particular interest in developing topical formulations of a JAK inhibitor for the treatment of inflammatory skin conditions.

In a preferred embodiment, the pharmaceutical compositions of the present invention comprise the JAK1 inhibitor, (3aR,5S,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide, which is also known as SHR0302 or ARQ-250. The pharmaceutical composition can include SHR0302 as a free base or a pharmaceutically acceptable salt. Suitable pharmaceutically acceptable salts can be found in Remington's Pharmaceutical Sciences, 17th ed., Mack Publishing Company (1985), which is incorporated by reference herein. In certain embodiments, the pharmaceutical composition comprises the bisulfite salt of SHR0302. The structure of SHR0302 is:

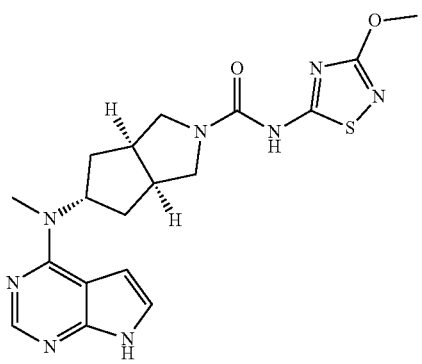 [SMILES: COc1nsc(NC(=O)N2C[C@H]3C[C@H](N(C)c4ncnc5[nH]ccc45)C[C@H]3C2)n1]

SHR0302 is a potent small molecule inhibitor of JAK 1 that has been shown to have a high selectively for JAK1 over JAK2, and thus has the potential to treat inflammatory diseases without causing the hematopoietic adverse effects, such as anemia, thrombocytopenia, and neutropenia, associated with JAK2 inhibition. It is contemplated that topical formulations comprising SHR0302 may be effective in the treatment of inflammatory skin diseases, disorders, and conditions including, but not limited to: atopic dermatitis, rosacea, psoriasis, seborrheic dermatitis, vitiligo, eczema, and alopecia areata.

The pharmaceutical compositions comprise a pharmaceutically effective amount of SHR0302. In certain embodiments, SHR0302 is present in an amount of about 0.01% w/w to about 7.5% w/w, or from about 0.01% w/w to about 5% w/w, or from about 0.1% w/w to about 3% w/w, or from about 0.01 to about 1.0% w/w, or from about 0.05 to about 1.0% w/w, or from about 0.1 to about 1.0% w/w, or from about 0.1 to about 0.6% w/w, or from about 0.1 to about 0.5% w/w. For example, the topical formulation comprises any of the following w/w percents of SHR0302: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

The pharmaceutical compositions of SHR0302 have a pH of less than about 4.6. In certain embodiments, the pharmaceutical compositions of SHR0302 have a pH of less than about 4.6, less than about 4.5, less than about 4.4, less than about 4.3, less than about 4.2, less than about 4.1, or less than about 4.0. In certain embodiments, the pharmaceutical compositions of SHR0302 have a pH between about 3.5 and about 4.6, between about 3.8 and about 4.6, between about 4.0 and about 4.6, between about 3.8 and about 4.2, between about 4.0 and about 4.6, between about 4.2 and about 4.6, between about 4.3 and about 4.6, or between about 4.4 and about 4.6. In certain embodiments, the pharmaceutical composition is formulated such that it has a pH of 3.5, 3.6, 3.7, 3.8, 3.9, 4.0, 4.1, 4.2, 4.3, 4.4, 4.5, or 4.6. In certain embodiments, the pharmaceutical composition is formulated such that it has a pH of about 4.0.

In certain embodiments, the inventors of the subject application have discovered that SHR0302 unexpectedly crystallizes in pharmaceutical compositions formulated at a pH above 4.6. Further, the inventors of the subject application have discovered that pharmaceutical compositions of SHR0302 formulated at a pH above 5.2 can exhibit loss of potency and reduced biological activity of the API. The pharmaceutical compositions of SHR0302 having a pH within the above-described ranges can exhibit improved stability and shelf life and reduced susceptibility to crystal formation of the API. The pharmaceutical formulations of SHR0302 can exhibit acceptable commercial product shelf life and do not exhibit loss of potency of the API after prolonged storage.

In certain embodiments, the pharmaceutical composition is stable for at least 6 months at controlled room temperature (i.e., 20 to 25° C.). In certain embodiments, the pharmaceutical composition is stable for at least 12 months at controlled room temperature. In certain embodiments the pharmaceutical composition is stable for at least 18 months at controlled room temperature. In certain embodiments, the pharmaceutical composition is stable for at least 6 months, at least 7 months, at least 8 months, at least 12 months, or at least 18 months at 30° C. In certain embodiments, the pharmaceutical composition is stable for at least 6 months, at least 7 months, at least 8 months, at least 12 months, or at least 18 months at 40° C.

In certain embodiments, the pharmaceutical composition can exhibit no crystal formation of the API after 6 months, 7 months, 8 months, 12 months, or 18 months of storage at controlled room temperature. In certain embodiments, the pharmaceutical composition can exhibit no crystal formation of the API after 6 months, 7 months, 8 months, 12 months, or 18 months of storage at 30° C. In certain embodiments, the pharmaceutical composition can exhibit no crystal formation of the API after 6 months, 7 months, 8 months, 12 months, or 18 months of storage at 40° C.

In certain embodiments, the pharmaceutical composition comprises laureth-4 (CAS number 5274-68-0) also known as tetraethylene glycol monododecyl ether, 3, 6, 9, 12-tetraoxatetracosan-1-ol, lauryl alcohol tri(oxyethylene) ethanol, PEG-4 lauryl ether, polyethylene glycol 200 lauryl ether, polyoxyethylene (4) lauryl ether, and tetraethylene glycol dodecyl ether. The compound has the molecular formula $C_{20}H_{42}O_5$ and has a molecular weight of 362.5 g/mol. Laureth-4 is a synthetic polymer that is commonly used as a surfactant and emulsifier in several personal care products, including cosmetics, shampoos, soaps, deodorants, and moisturizing products. Laureth-4 can act as a skin penetration enhancer in the topical formulations of the present invention. In certain embodiments, the laureth-4 is present in an amount of about 0.05 to about 8.0% w/w, about 0.1 to about 6.0% w/w, about 0.5 to about 5.0% w/w, about 1.0 to about 4.0% w/w, or about 2.0 to about 4.0% w/w. In certain embodiments, laureth-4 is present in amount of about 0.05% w/w, 0.10% w/w, 0.15% w/w, 0.20% w/w, 0.25% w/w, 0.50% w/w, 0.75% w/w, 1.0% w/w, 1.25% w/w, 1.50% w/w, 1.75% w/w, 2.0% w/w, 2.25% w/w, 2.50% w/w, 2.75% w/w, 3.0% w/w, 3.25% w/w, 3.50% w/w, 3.75% w/w, 4.0% w/w, 4.25% w/w, 4.50% w/w, 4.75% w/w, 5.0% w/w, 5.25% w/w, 5.50% w/w, 5.75% w/w, or 6.0% w/w.

In certain embodiments, the inventors of the subject application have also discovered that SHR0302 unexpectedly crystallizes in pharmaceutical compositions formulated with high concentrations of dimethyl sulfoxide (DMSO). Further, the inventors of the subject application have discovered that pharmaceutical compositions of SHR0302 comprising less than about 30% of dimethyl sulfoxide have improved stability and do no exhibit crystal formation of the API. In certain embodiments, the pharmaceutical composition comprises dimethyl sulfoxide (DMSO). In certain embodiments, DMSO is present in an amount of about 5% to about 30% w/w, about 10% to about 30% w/w, about 10% to about 27% w/w, about 10% to about 25%, about 15% to about 30% w/w, about 15% to about 27% w/w, about 15% to about 25% w/w, about 20% to about 30% w/w, about 20% to about 27% w/w, or about 20% to about 25% w/w. In certain embodiments, DMSO is present in amount of about 5% w/w, 7.5% w/w, 10% w/w, 12.5% w/w, 15% w/w, 17.5% w/w, 20% w/w, 21% w/w, 22% w/w, 22.5% w/w, 23% w/w, 24% w/w, 25% w/w, 26% w/w, 27% w/w, 27.5% w/w, 28% w/w, 29% w/w, or 30% w/w. In certain embodiments, DMSO is present in an amount of about 20%, 25%, or 30% w/w.

Preferably the topical formulations of the present invention are in one of the following forms:

An oil-in-water emulsion: The product may be an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) to help to stabilize the emulsion.

A hydrophilic or hydrophobic ointment: The compositions are formulated with a hydrophobic base (e.g. petrolatum, thickened or gelled water insoluble oils, and the like) and optionally have a minor amount of a water soluble phase. Hydrophilic ointments generally contain one or more surfactants or wetting agents A microemulsion: These are clear, thermodynamically stable isotropic liquid systems that contain oil, water and surfactants, frequently in combination with a cosurfactant. Microemulsions may be water continuous, oil continuous or bicontinuous mixtures. The formulations may optionally also contain water up to 60% by weight. Higher levels may be suitable in some compositions.

A nanoemulsion: These are isotropic dispersed systems that contain water, oil, and an emulsifier. The system may be an oily system dispersed in an aqueous system, or an aqueous system dispersed in an oily system forming droplets or oily phases of nanometric sizes. Nanoemulsions often have higher loading capacity for lipophilic active ingredients than microemulsions. Hydrophobic and hydrophilic active ingredients can also be formulated in nanoemulsion. Nanoemulsions may be formed by any suitable method known in the art, including high-pressure homogenization, microfluidization, and phase-inversion temperature.

An aerosol foam or spray: The product may be an alcohol/solvent based solution containing an emulsifying wax or an emulsion comprising a discrete phase of a hydrophobic component and a continuous aqueous phase that includes water and optionally one or more polar hydrophilic excipients as well as solvents, co-solvents, surfactants, emulsifiers, and other components. These solvent or emulsion foam concentrates may include water-soluble or water-swellable polymers that help to stabilize the emulsion and corrosion inhibitors to improve compatibility between the formulation and the package. A hydrocarbon, hydrochlorofluorocarbon (HCFC) or chlorofluorocarbon (CFC) aerosol propellant can be added to the solvent or emulsion foam concentrate in packaging designed to maintain pressure until the foam or spray product is dispensed for application.

In certain embodiments, the pharmaceutical compositions can contain one or more of the following excipients.

Solvents

Compositions according to the present invention may include one or more solvents or co-solvents which modify skin permeation or the activity of other excipients contained in the formulation. Solvents include, but are not limited to acetone, ethanol, benzyl alcohol, butyl alcohol, diethyl sebacate, diethylene glycol monoethyl ether, diisopropyl adipate, dimethyl isosorbide, dimethyl sulfoxide, ethyl acetate, isopropyl alcohol, isopropyl isostearate, isopropyl myristate, isopropyl palmitate, N-methyl pyrrolidinone, polyethylene glycol (e.g., PEG 200), glycerol, propylene glycol and SD alcohol.

Surfactants

Compositions according to the present invention may include one or more surfactants or co-surfactants. Surfactants include, but are not limited to short-chain alcohols, alkane diols and triols, alkyl phosphate esters, polyethylene glycols and glycol ethers, polyethylene stearyl ethers, including those sold under the tradenames Brij S2, Brij S20, Brij 721, Brij 38, Brij 52, Brij 56, and Brij W1, pyrrolidine derivatives, bile salts, sorbitan fatty acid esters and polyoxyethylene sorbitan fatty acid esters.

Polymeric Emulsifiers

Compositions for use in the present invention may include one or more polymeric emulsifier. Polymeric emulsifiers can include high molecular weight copolymers of acrylic acid and $C_{10-30}$ alkyl acrylate crosslinked with allyl pentaerythritol. Polymeric emulsifiers particularly suitable for use with the methods of the present invention include those marketed under the tradename Pemulen™ and sold by Lubrizol, including Pemulen™ TR-1 and Pemulen™ TR-2 NF.

Moisturizers

Compositions according to the present invention may include one or more moisturizers to increase the level of hydration. The moisturizer can be a hydrophilic material including humectants or it can be a hydrophobic material including emollients. Suitable moisturizers include, but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, elastomers, ethylhexyl hydroxystearate, fatty acids, glyceryl isostearate, glyceryl laurate, glyceryl monostearate, glyceryl oleate, glyceryl palmitate, glycol distearate, glycol stearate, isopropyl palmitate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, ST-Elastomer 10 (a mixture of high molecular weight crosslinked silicone (12%) in decamethycyclopentasiloxane (D5)), polypropylene glycol stearyl ethers, and stearyl alcohol.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, acrylamide/sodium acryloyldimethyl taurate copolymer, carboxy vinyl copolymer, carboxymethylcellulose, carboxypolymethylene, carrageenan, guar gum, xanthan gum, hydroxyethyl cellulose, hydroxypropyl cellulose, microcrystalline wax, and methylcellulose. In certain embodiments, the pharmaceutical formulation can include carbomers such as Carbopol 974P or Carbomer Homopoylmer Type B USP. In certain embodiments, the pharmaceutical formulation can comprise Sepineo P600 (acrylaminde/sodium acryloyldimethyl taurate copolymer/isohexadecane and polysorbate 80).

Additional Components

Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol, methylparaben, propylparaben), antioxidants (e.g., BHT, BHA, ascorbic acid, tocopherol, citric acid, propyl gallate, sodium metabisulfite), sequestering agents, stabilizers, buffers, pH adjusting agents (preferably agents which result in an acidic pH, including but not limited to gluconolatone, citric acid, lactic acid, and alpha hydroxyacids), skin penetration enhancers, skin protectants (including but not limited to petrolatum, paraffin wax, dimethicone, glyceryl monoisostearate, isopropyl isostearate, isostearyl isostearate, cetyl alcohol, potassium cetyl phosphate, cetyl behenate and behenic acid), chelating agents, film formers, suspending agents (e.g., xanthan gum), dyes, pigments, diluents, bulking agents, fragrances, aerosol producing agents and other excipients to improve the stability or aesthetics, may be added to the composition.

Compositions according to the present invention may be formulated with additional active agents depending on the conditions being treated. Exemplary additional active agents for a combination topical drug product include corticosteroids (e.g., clobetasol, betamethasone, halobetasol, or triamcinolone), beta andrenergic antagonists (e.g., timolol), calcineurin inhibitors (e.g., tacrolimus, or pimecrolimus), methotrexate, or cyclosporine.

Example Formulations

In certain embodiments, the topical pharmaceutical composition comprises a pharmaceutically effective amount of SHR0302, laureth-4, and dimethyl sulfoxide. In certain embodiments, the pharmaceutical composition comprises an amount of about 0.1 to about 1.0% w/w of SHR0302. In certain embodiments, the pharmaceutical composition comprises an amount of about 0.5% to about 5% w/w of laureth-4. In certain embodiments, the pharmaceutical composition comprises an amount of about 20% to about 27% w/w of dimethyl sulfoxide.

In certain embodiments, the topical pharmaceutical composition comprises a pharmaceutically effective amount of SHR0302 and one or more of dimethyl sulfoxide, laureth-4, butylated hydroxytoluene, benzyl alcohol, propylene glycol, polyethylene glycol 200, cyclomethicone, dimethicone, ST-Elastomer 10, Pemulen TR 1, Carbopol 974P, and a pH adjusting agent. In certain embodiments, the pharmaceutical composition comprises an amount of about 0.1 to about 1.0% w/w of SHR0302. In certain embodiments, the pharmaceutical composition comprises an amount of about 20% to about 40% w/w of dimethyl sulfoxide. In certain embodiments, the pharmaceutical composition comprises an amount of about 0.5% to about 5% w/w of laureth-4. In certain embodiments, the pharmaceutical composition comprises an amount of about 0.01% to about 5% w/w of butylated hydroxytoluene. In certain embodiments, the pharmaceutical composition comprises an amount of about 0.5% to about 5% w/w of benzyl alcohol. In certain embodiments, the pharmaceutical composition comprises an amount of about 5% to about 20% w/w of propylene glycol. In certain embodiments, the pharmaceutical composition comprises an amount of about 5% to about 20% w/w of polyethylene glycol 200. In certain embodiments, the pharmaceutical composition comprises an amount of about 5% to about 10% w/w of cyclomethicone. In certain embodiments, the pharmaceutical composition comprises an amount of about 0.5% to about 5% w/w of dimethicone. In certain embodiments, the pharmaceutical composition comprises an amount of about 0.5% to about 5% w/w of ST-Elastomer 10. In certain embodiments, the pharmaceutical composition comprises an amount of about 0.1 to about 1.0% w/w of Pemulen TR 1. In certain embodiments, the pharmaceutical composition comprises an amount of about 0.1 to about 1.5% w/w of Carbopol 974P.

In another exemplary embodiment, the topical pharmaceutical composition comprises a pharmaceutically effective amount of SHR0302 and one or more of N-methyl-2 pyrrolidone, laureth-4, butylated hydroxytoluene, methylparaben, propylparaben, Crodafos CES, isopropyl palmitate, white petrolatum, propylene glycol, polyethylene glycol 200, a pH adjusting agent, and xanthan gum. Crodafos CES is an emulsifier blend of cetearyl alcohol, dicetyl phosphate, and ceteth-10 phosphate, which is manufactured by Croda. Crodafos™ CES PHARMA is manufactured using the same starting materials and process, but undergoes enhanced quality control and release testing and uses the nomenclature cetearyl alcohol, cetearyl phosphate and ceteareth-10 phosphate in keeping with standard practice for naming pharmaceutical excipients. This commercially available emulsifier blend is a self-emulsifying wax that is predominately the waxy material cetearyl alcohol (which is a mixture of cetyl alcohol ($C_{16}H_{34}O$) and stearyl alcohol ($C_{18}H_{38}O$)) combined with 10-20% dicetyl phosphate (cetearyl phosphate) and 10-20% ceteth-10 phosphate (ceteareth-10 phosphate). In certain embodiments, the pharmaceutical composition comprises an amount of about 0.1 to about 1.0% w/w of SHR0302. In certain embodiments, the pharmaceutical composition comprises an amount of about 15% to about 40% w/w of N-methyl-2 pyrrolidone. In certain embodiments, the pharmaceutical composition comprises an amount of about 0.5% to about 5% w/w of laureth-4. In certain embodiments, the pharmaceutical composition comprises an amount of about 0.01% to about 5% w/w of butylated hydroxytoluene. In certain embodiments, the pharmaceutical composition comprises an amount of about 0.01% to about 5% w/w of methylparaben. In certain embodiments, the pharmaceutical composition comprises an amount of about 0.01% to about 5% w/w of propylparaben. In certain embodiments, the pharmaceutical composition comprises an amount of about 5% to about 20% w/w of Crodafos CES. In certain embodiments, the pharmaceutical composition comprises an amount of about 1% to about 10% w/w of isopropyl palmitate. In certain embodiments, the pharmaceutical composition comprises an amount of about 1% to about 10% w/w of white petrolatum. In certain embodiments, the pharmaceutical composition comprises an amount of about 5% to 20% w/w of propylene glycol. In certain embodiments, the pharmaceutical composition comprises an amount of about 5% to 20% w/w of polyethylene glycol 200.

Administration and Dosage

The compositions according to the present invention can be administered by any suitable administration route including but not limited to cutaneously (topically), transdermally, and mucosally. In a preferred embodiment, the composition is administered topically. The composition can be administered one or more times per month, one or more times per week, or one or more times per day. In preferred embodiments, the compositions are administered one, two, or three times per day.

In certain embodiments, the topical formulations comprising laureth-4 that are disclosed herein can result in improved skin permeation. As disclosed in U.S. patent application Ser. No. 17/443,699, which is incorporated by reference herein, pharmaceutical compositions comprising laureth-4 can result in a 5-fold to 30-fold increase in skin permeation as compared to the same topical formulation without laureth-4 as measured by in vitro permeation testing (IVPT). In preferred embodiments, the topical formulation containing laureth-4 products a greater than 5-fold, greater than 8-fold, greater than 10-fold, greater than 15-fold, or greater than 20-fold increase in skin permeation compared to the same topical formulation without laureth-4.

EXAMPLES

While various embodiments have been described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Example 1

A single batch of the pharmaceutical composition (Formulation A) set forth in Table 1 was prepared. The batch pH was increased incrementally from an initial pH of 4.31 to a final pH of 6.53. A sample was taken at each iteration having a different pH.

TABLE 1

(Formulation A)

| Material | Formula (% w/w) |
|---|---|
| ARQ 250 (SHR0302) Sulfate Salt | 0.3 |
| Dimethyl Sulfoxide | 30.0 |
| Benzyl Alcohol | 2.0 |
| Butylated Hydroxytoluene | 0.05 |
| Cyclomethicone | 7.00 |
| Dow Corning ® ST-Elastomer 10 | 2.00 |
| Dimethicone, 350 cst | 1.00 |
| Propylene Glycol | 15.0 |
| D-Limonene | 0.1 |
| Polyethylene Glycol 200 (PEG 200) | 15.0 |
| Edetate Disodium, Dihydrate | 0.05 |
| Carbomer Copolymer (Pemulen ™ TR-1) | 0.8 |
| Carbopol ® 974P Polymer (Carbomer Homopolymer) | 1.5 |
| 25% w/w Trolamine Solution | pH to 5.5 ± 0.4 |
| Sterile Water for Irrigation | 25.2 |

A stability study was conducted using each of the samples of the formulation in Table 1 having a different pH. The stability of each sample was observed at controlled room temperature, 30° C., and 40° C. for up to 12 months. After initial preparation and after each month thereafter for up to 12 months (i.e., at time of 0 (initial), 1 month, 2 months, 3 months, 4 months, 5 months, 6 months, 7 months, 8 months, 9 months, 10 months, 11 months, and 12 months), the samples were investigated for the presence of crystals. In particular, the sample was visually examined with a magnifying glass with an integrated light to assess whether crystals were present. The same sample was used for inspection as the inspection was non-destructive. A spatula was used to disturb each sample during inspection. The inspection was at all depths of the vial.

The results of the stability study are set forth below in Table 2 (data for months 0 to 6) and Table 3 (data for months 7 to 12).

TABLE 2

(Data for 0-6 Months)

| | | Crystal Observed (Yes/No) | | | | | | |
|---|---|---|---|---|---|---|---|---|
| pH of Formulation | Storage Condition | T = 0 | T = 1 M | T = 2 M | T = 3 M | T = 4 M | T = 5 M | T = 6 M |
| Initial pH 4.31 | Controlled Room Temp. | No | No | No | No | No | No | No |
| | 30° | No | N/A | No | No | No | No | No |
| | 40° | No | No | No | No | No | No | No |
| pH 4.39 | Controlled Room Temp. | No | No | No | No | No | No | No |
| | 30° | No | N/A | No | No | No | No | No |
| | 40° | No | No | No | No | No | No | No |
| pH 4.57 | Controlled Room Temp. | No | No | No | No | No | No | No |
| | 30° | No | N/A | No | No | No | No | No |
| | 40° | No | No | No | No | No | No | No |
| pH 4.97 | Controlled Room Temp. | No | No | No | No | No | No | Yes |
| | 30° | No | N/A | No | No | No | No | No |
| | 40° | No | No | No | No | No | Yes | Yes |
| pH 5.13 | Controlled Room Temp. | No | No | No | No | No | No | Yes |
| | 30° | No | N/A | No | No | No | No | Yes |
| | 40° | No | No | No | No | No | Yes | Yes |
| pH 5.53 | Controlled Room Temp. | No | No | No | No | Yes | Yes | Yes |
| | 30° | No | N/A | No | Yes | Yes | Yes | Yes |
| | 40° | No | No | No | Yes | Yes | Yes | Yes |
| pH 5.72 | Controlled Room Temp. | No | No | No | No | Yes | Yes | Yes |
| | 30° | No | N/A | No | Yes | Yes | Yes | Yes |
| | 40° | No | No | No | Yes | Yes | Yes | Yes |
| pH 5.90 | Controlled Room Temp. | No | No | No | No | Yes | Yes | Yes |
| | 30° | No | N/A | No | Yes | Yes | Yes | Yes |
| | 40° | No | No | No | Yes | Yes | Yes | Yes |
| pH 6.53 | Controlled Room Temp. | No | No | Yes | Yes | Yes | Yes | Yes |
| | 30° | No | N/A | Yes | Yes | Yes | Yes | Yes |
| | 40° | No | Yes | Yes | Yes | Yes | Yes | Yes |

TABLE 3

(Data for 7-12 months)

| | | Crystal Observed (Yes/No) | | | | | |
|---|---|---|---|---|---|---|---|
| pH of Formulation | Storage Condition | T = 7 M | T = 8 M | T = 9 M | T = 10 M | T = 11 M | T = 12 M |
| Initial pH 4.31 | Controlled Room Temp. | No | No | No | No | No | No |
| | 30° | No | No | No | No | No | No |
| | 40° | No | No | No | No | No | Yes |
| pH 4.39 | Controlled Room Temp. | No | No | No | No | No | No |
| | 30° | No | No | No | No | No | No |
| | 40° | No | No | No | No | No | Yes |
| pH 4.57 | Controlled Room Temp. | No | No | No | No | No | No |
| | 30° | No | No | No | No | No | No |
| | 40° | No | No | No | No | No | Yes |
| pH 4.97 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.13 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.53 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.72 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.90 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.53 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |

As illustrated in Tables 2 and 3, the stability of the formulation decreased as the pH increased. The pharmaceutical compositions formulated at a pH of 4.31, 4.39, and 4.57 did not exhibit any crystal formation at controlled room temperature or 30° C. for the duration of the study (i.e., 12 months). Further, these pharmaceutical compositions did not exhibit any crystal formation at 40° C. through 11 months.

The inventors of the subject application also observed a loss of potency due to assay loss in formulations having a pH of 4.6 or greater under intermediate and/or accelerated conditions. None of the batches with a pH equal to or lower than 4.6 were found to show loss of potency due to assay loss.

Example 2

A single batch of a first pharmaceutical composition similar to the composition forth in Table 1 but with 4% laureth-4 was prepared (Formulation B). The batch pH of Formulation B was increased incrementally from an initial pH of 4.57 to a final pH of 6.59. A sample was taken at each iteration having a different pH.

A single batch of a second pharmaceutical composition was prepared similar to the composition set forth in Table 1 but with 4% laureth-4 and 25% dimethyl sulfoxide (DMSO) instead of 30% dimethyl sulfoxide (DMSO) (Formulation C). The batch pH of Formulation C was increased incrementally from an initial pH of 4.45 to a final pH of 6.61. A sample was taken at each iteration having a different pH.

A stability study was conducted using each of the samples of Formulations B and C having a different pH. The stability of each sample was observed at controlled room temperature, 30° C., and 40° C. for up to 12 months. After initial preparation and after each month thereafter for up to 8 months (i.e., at time of 0 (initial), 1 month, 2 months, 3 months, 4 months, 5 months, 6 months, 7 months, 8 months, 9 months, 10 months, 11 months, and 12 months), the samples were investigated for the presence of crystals. In particular, the sample was visually examined with a magnifying glass with an integrated light to assess whether crystals were present. The same sample was used for inspection as the inspection was non-destructive. A spatula was used to disturb each sample during inspection. The inspection was at all depths of the vial.

The results of the stability study are set forth below in Tables 4 (data for 0-6 months) and 5 (data for 7-12 months) for Formulation B and Tables 6 (data for 0-6 months) and 7 (data for 7-12 months) for Formulation C.

TABLE 4

(Data for Formulation B, 0-6 months)

| | | Crystal Observed (Yes/No) | | | | | | |
|---|---|---|---|---|---|---|---|---|
| pH of Formulation | Storage Condition | T = 0 | T = 1 M | T = 2 M | T = 3 M | T = 4 M | T = 5 M | T = 6 M |
| Initial pH 4.57 | Controlled Room Temp. | No | No | No | No | No | No | No |
| | 30° | No | No | No | No | No | No | No |
| | 40° | No | No | No | No | No | No | No |
| pH 4.85 | Controlled Room Temp. | No | No | No | No | No | No | No |
| | 30° | No | No | No | No | No | No | No |
| | 40° | No | No | No | No | No | No | No |
| pH 5.07 | Controlled Room Temp. | No | No | No | No | No | No | No |
| | 30° | No | No | No | No | No | No | No |
| | 40° | No | No | No | No | No | Yes | Yes |
| pH 5.24 | Controlled Room Temp. | No | No | No | No | Yes | Yes | Yes |
| | 30° | No | No | No | No | Yes | Yes | Yes |
| | 40° | No | No | No | No | Yes | Yes | Yes |

TABLE 4-continued (Data for Formulation B, 0-6 months)

| pH of Formulation | Storage Condition | Crystal Observed (Yes/No) | | | | | | |
|---|---|---|---|---|---|---|---|---|
| | | T = 0 | T = 1 M | T = 2 M | T = 3 M | T = 4 M | T = 5 M | T = 6 M |
| pH 5.55 | Controlled Room Temp. | No | No | No | Yes | Yes | Yes | Yes |
| | 30° | No | No | No | Yes | Yes | Yes | Yes |
| | 40° | No | No | No | Yes | Yes | Yes | Yes |
| pH 5.87 | Controlled Room Temp. | No | No | No | Yes | Yes | Yes | Yes |
| | 30° | No | No | Yes | Yes | Yes | Yes | Yes |
| | 40° | No | No | Yes | Yes | Yes | Yes | Yes |
| pH 6.05 | Controlled Room Temp. | No | No | No | Yes | Yes | Yes | Yes |
| | 30° | No | No | Yes | Yes | Yes | Yes | Yes |
| | 40° | No | No | Yes | Yes | Yes | Yes | Yes |
| pH 6.29 | Controlled Room Temp. | No | No | Yes | Yes | Yes | Yes | Yes |
| | 30° | No | No | Yes | Yes | Yes | Yes | Yes |
| | 40° | No | No | Yes | Yes | Yes | Yes | Yes |
| pH 6.59 | Controlled Room Temp. | No | No | Yes | Yes | Yes | Yes | Yes |
| | 30° | No | No | Yes | Yes | Yes | Yes | Yes |
| | 40° | No | No | Yes | Yes | Yes | Yes | Yes |

TABLE 5

(Data for Formulation B, 7-12 months)

| pH of Formulation | Storage Condition | Crystal Observed (Yes/No) | | | | | |
|---|---|---|---|---|---|---|---|
| | | T = 7 M | T = 8 M | T = 9 M | T = 10 M | T = 11 M | T = 12 M |
| Initial pH 4.57 | Controlled Room Temp. | No | No | No | No | No | No |
| | 30° | No | No | No | No | No | No |
| | 40° | No | No | No | No | No | No |
| pH 4.85 | Controlled Room Temp. | No | No | No | Yes | Yes | Yes |
| | 30° | No | No | No | No | Yes | Yes |
| | 40° | No | No | Yes | Yes | Yes | Yes |
| pH 5.07 | Controlled Room Temp. | No | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.24 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.55 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 5.87 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.05 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.29 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.59 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |

TABLE 6

(Data for Formulation C, 0-6 months)

| pH of Formulation | Storage Condition | Crystal Observed (Yes/No) | | | | | | |
|---|---|---|---|---|---|---|---|---|
| | | T = 0 | T = 1 M | T = 2 M | T = 3 M | T = 4 M | T = 5 M | T = 6 M |
| Initial pH 4.45 | Controlled Room Temp. | No | No | No | No | N/A | No | No |
| | 30° | No | No | No | No | N/A | No | No |
| | 40° | No | No | No | No | N/A | No | No |
| pH 4.86 | Controlled Room Temp. | No | No | No | No | N/A | No | No |
| | 30° | No | No | No | No | N/A | No | No |
| | 40° | No | No | No | No | N/A | No | No |
| pH 5.05 | Controlled Room Temp. | No | No | No | No | N/A | No | No |

TABLE 6-continued (Data for Formulation C, 0-6 months)

| pH of Formulation | Storage Condition | Crystal Observed (Yes/No) | | | | | | |
|---|---|---|---|---|---|---|---|---|
| | | T = 0 | T = 1 M | T = 2 M | T = 3 M | T = 4 M | T = 5 M | T = 6 M |
| | 30° | No | No | No | No | N/A | No | No |
| | 40° | No | No | No | No | N/A | No | No |
| pH 5.29 | Controlled Room Temp. | No | No | No | No | N/A | No | No |
| | 30° | No | No | No | No | N/A | No | No |
| | 40° | No | No | No | No | N/A | No | No |
| pH 5.55 | Controlled Room Temp. | No | No | No | No | N/A | No | No |
| | 30° | No | No | No | No | N/A | No | No |
| | 40° | No | No | No | No | N/A | No | No |
| pH 5.76 | Controlled Room Temp. | No | No | No | No | N/A | No | No |
| | 30° | No | No | No | No | N/A | No | No |
| | 40° | No | No | No | No | N/A | No | No |
| pH 6.03 | Controlled Room Temp. | No | No | No | No | N/A | No | No |
| | 30° | No | No | No | No | N/A | No | No |
| | 40° | No | No | No | No | N/A | No | No |
| pH 6.23 | Controlled Room Temp. | No | No | No | No | N/A | No | No |
| | 30° | No | No | No | No | N/A | No | No |
| | 40° | No | No | No | No | N/A | No | No |
| pH 6.61 | Controlled Room Temp. | No | No | No | No | N/A | No | No |
| | 30° | No | No | No | No | N/A | No | No |
| | 40° | No | No | No | No | N/A | No | No |

TABLE 7

(Data for Formulation C, 7-12 months)

| pH of Formulation | Storage Condition | Crystal Observed (Yes/No) | | | | | |
|---|---|---|---|---|---|---|---|
| | | T = 7 M | T = 8 M | T = 9 M | T = 10 M | T = 11 M | T = 12 M |
| Initial pH 4.45 | Controlled Room Temp. | No | No | No | No | No | No |
| | 30° | Yes | Yes | Yees | Yes | Yes | Yes |
| | 40° | Yes | Yes | Yes | Yes | Yes | Yes |
| pH 4.86 | Controlled Room Temp. | No | No | Yes | Yes | Yes | Yes |
| | 30° | Yes | Yes | Yes | Yes | Yes | Yes |
| | 40° | Yes | Yes | Yes | Yes | Yes | Yes |
| pH 5.05 | Controlled Room Temp. | No | No | Yes | Yes | Yes | Yes |
| | 30° | Yes | Yes | Yes | Yes | Yes | Yes |
| | 40° | Yes | Yes | Yes | Yes | Yes | Yes |
| pH 5.29 | Controlled Room Temp. | No | No | Yes | Yes | Yes | Yes |
| | 30° | Yes | Yes | Yes | Yes | Yes | Yes |
| | 40° | Yes | Yes | Yes | Yes | Yes | Yes |
| pH 5.55 | Controlled Room Temp. | No | No | Yes | Yes | Yes | Yes |
| | 30° | No | No | Yes | Yes | Yes | Yes |
| | 40° | Yes | Yes | Yes | Yes | Yes | Yes |
| pH 5.76 | Controlled Room Temp. | No | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.03 | Controlled Room Temp. | No | Yes | Yes | Yes | Yes | Yes |
| | 30° | Yes | Yes | Yes | Yes | Yes | Yes |
| | 40° | Yes | Yes | Yes | Yes | Yes | Yes |
| pH 6.23 | Controlled Room Temp. | No | Yes | Yes | Yes | Yes | Yes |
| | 30° | No | Yes | Yes | Yes | Yes | Yes |
| | 40° | Yes | Yes | Yes | Yes | Yes | Yes |
| pH 6.61 | Controlled Room Temp. | Yes | Yes | Yes | Yes | Yes | Yes |
| | 30° | Yes | Yes | Yes | Yes | Yes | Yes |
| | 40° | Yes | Yes | Yes | Yes | Yes | Yes |

As illustrated in Tables 4-7, the stability of the formulation comprising 25% DMSO (Formulation C) was improved relative to the formulation comprising 30% DMSO (Formulation B). Formulation C formulated at all pH values except for pH 6.61 did not exhibit any crystal formation at controlled room temperature for the first seven months of the study. Moreover, Formulation C formulated at all pH values of 5.55 and below did not exhibit any crystal formation at controlled room temperature for the first 8 months of the study. Further, Formulation C formulated at all pH values did not exhibit any crystal formation at 30° C. or 40° C. for the first 6 months of the study.

Example 3

Five different batches of pharmaceutical compositions were prepared. A single batch of the first pharmaceutical composition similar to Formulation B but with Sepineo P600 and no EDTA was prepared (Formulation D). A single batch of a second pharmaceutical composition similar to Formulation D but with free base SHR0302 instead of the sulfate salt of SHR0302 was prepared (Formulation E). A single batch of a third pharmaceutical composition similar to Formulation B but with no EDTA was prepared (Formulation F). A single batch of a fourth pharmaceutical composition similar to Formulation F but with free base SHR0302 instead of the sulfate salt of SHR0302 was prepared (Formulation G). A single batch of a fifth pharmaceutical composition similar to formulation C but with no EDTA and the free base SHR0302 instead of the sulfate salt of SHR0302 was prepared (Formulation H). The batch pH of Formulations D, E, F, G, and H was increased incrementally as set forth in Tables 8-17 below. A sample was taken at each iteration having a different pH.

A stability study was conducted using each of the samples of Formulations D, E, F, G, and H having a different pH. The stability of each sample was observed at controlled room temperature, 30° C., and 40° C. for up to 9 months. After initial preparation and after each month thereafter for up to 9 months (i.e., at time 1 month, 2 months, 3 months, 4 months, 5 months, 6 months, 7 months, 8 months, and 9 months), the samples were investigated for the presence of crystals. In particular, the sample was visually examined with a magnifying glass with an integrated light to assess whether crystals were present. The same sample was used for inspection as the inspection was non-destructive. A spatula was used to disturb each sample during inspection. The inspection was at all depths of the vial.

The results of the stability study are set forth below in Table 8 (data for Formulation D, Months 1-4), Table 9 (data for Formulation D, Months 5-9), Table 10 (data for Formulation E, Months 1-4), Table 11 (data for Formulation E, Months 5-9), Table 12 (data for Formulation F, Months 1-4), Table 13 (data for Formulation F, Months 5-9), Table 14 (data for Formulation G, Months 1-4), Table 15 (data for Formulation G, Months 5-9), Table 16 (data for Formulation H, Months 1-4), and Table 17 (data for Formulation H, Months 5-9).

TABLE 8

(Data for Formulation D, Months 1-4)

| | | Crystal Observed (Yes/No) | | | |
|---|---|---|---|---|---|
| pH of Formulation | Storage Condition | T = 1 M | T = 2 M | T = 3 M | T = 4 M |
| Initial pH 4.21 | Controlled Room Temp. | No | No | No | No |
| | 30° | No | No | No | No |
| | 40° | No | No | No | No |
| pH 4.49 | Controlled Room Temp. | No | No | No | No |
| | 30° | No | No | No | No |
| | 40° | No | No | No | No |
| pH 4.78 | Controlled Room Temp. | No | No | No | No |
| | 30° | No | No | No | No |
| | 40° | No | No | No | No |
| pH 5.41 | Controlled Room Temp. | Yes | Yes | Yes | Yes |
| | 30° | No | Yes | Yes | Yes |
| | 40° | Yes | Yes | Yes | Yes |

TABLE 9

(Data for Formulation D, Months 5-9)

| | | Crystal Observed (Yes/No) | | | | |
|---|---|---|---|---|---|---|
| pH of Formulation | Storage Condition | T = 5 M | T = 6 M | T = 7 M | T = 8 M | T = 9 M |
| Initial pH 4.21 | Controlled Room Temp. | No | No | No | No | No |
| | 30° | No | No | No | No | No |
| | 40° | No | No | No | No | No |
| pH 4.49 | Controlled Room Temp. | No | No | No | No | No |
| | 30° | No | No | No | No | No |
| | 40° | No | No | No | No | No |
| pH 4.78 | Controlled Room Temp. | No | No | No | No | No |
| | 30° | No | No | No | No | No |
| | 40° | No | No | No | No | No |
| pH 5.41 | Controlled Room Temp. | Yes | Yes | Yes | Yes | Yes |
| | 30° | Yes | Yes | Yes | Yes | Yes |
| | 40° | Yes | Yes | Yes | Yes | Yes |

TABLE 10

(Data for Formulation E, Months 1-4)

| | | Crystal Observed (Yes/No) | | | |
|---|---|---|---|---|---|
| pH of Formulation | Storage Condition | T = 1 M | T = 2 M | T = 3 M | T = 4 M |
| Initial pH 4.18 | Controlled Room Temp. | No | No | No | No |
| | 30° | No | No | No | No |
| | 40° | No | No | No | No |
| pH 4.40 | Controlled Room Temp. | No | No | No | No |
| | 30° | No | No | No | No |
| | 40° | No | No | No | No |
| pH 4.82 | Controlled Room Temp. | No | No | No | No |
| | 30° | No | Yes | Yes | Yes |
| | 40° | No | No | Yes | Yes |
| pH 5.42 | Controlled Room Temp. | Yes | Yes | Yes | Yes |
| | 30° | Yes | Yes | Yes | Yes |
| | 40° | Yes | Yes | Yes | Yes |

TABLE 11

(Data for Formulation E, Months 5-9)

| | | Crystal Observer (Yes/No) | | | | |
|---|---|---|---|---|---|---|
| pH of Formulation | Storage Condition | T = 5 M | T = 6 M | T = 7 M | T = 8 M | T = 9 M |
| Initial pH 4.18 | Controlled Room Temp. | No | No | No | No | No |
| | 30° | No | No | No | No | No |
| | 40° | No | No | No | No | No |
| pH 4.40 | Controlled Room Temp. | No | No | No | No | No |
| | 30° | No | No | No | No | No |
| | 40° | No | No | Yes | Yes | Yes |
| pH 4.82 | Controlled Room Temp. | Yes | Yes | Yes | Yes | Yes |
| | 30° | Yes | Yes | Yes | Yes | Yes |
| | 40° | Yes | Yes | Yes | Yes | Yes |
| pH 5.42 | Controlled Room Temp. | Yes | Yes | Yes | Yes | Yes |
| | 30° | Yes | Yes | Yes | Yes | Yes |
| | 40° | Yes | Yes | Yes | Yes | Yes |

TABLE 12

(Data for Formulation F, Months 1-4)

| pH of Formulation | Storage Condition | Crystal Observed (Yes/No) | | | |
|---|---|---|---|---|---|
| | | T = 1 M | T = 2 M | T = 3 M | T = 4 M |
| Initial pH 4.25 | Controlled Room Temp. | No | No | No | No |
| | 30° | No | No | No | No |
| | 40° | No | No | No | No |
| pH 4.56 | Controlled Room Temp. | No | No | No | No |
| | 30° | No | No | No | No |
| | 40° | No | No | No | No |
| pH 4.81 | Controlled Room Temp. | No | No | No | No |
| | 30° | No | No | No | No |
| | 40° | No | No | No | No |
| pH 5.27 | Controlled Room Temp. | No | No | No | No |
| | 30° | No | No | No | Yes |
| | 40° | No | No | No | Yes |

TABLE 13

(Data for Formulation F, Months 5-9)

| pH of Formulation | Storage Condition | Crystal Observer (Yes/No) | | | | |
|---|---|---|---|---|---|---|
| | | T = 5 M | T = 6 M | T = 7 M | T = 8 M | T = 9 M |
| Initial pH 4.25 | Controlled Room Temp. | No | No | No | No | No |
| | 30° | No | No | No | No | No |
| | 40° | No | No | No | No | No |
| pH 4.56 | Controlled Room Temp. | No | No | No | No | No |
| | 30° | No | No | No | No | No |
| | 40° | No | No | No | No | No |
| pH 4.81 | Controlled Room Temp. | No | No | No | No | No |
| | 30° | No | No | No | No | No |
| | 40° | No | No | No | No | No |
| pH 5.27 | Controlled Room Temp. | No | Yes | Yes | Yes | Yes |
| | 30° | Yes | Yes | Yes | Yes | Yes |
| | 40° | Yes | Yes | Yes | Yes | Yes |

TABLE 14

(Data for Formulation G, Months 1-4)

| pH of Formulation | Storage Condition | Crystal Observed (Yes/No) | | | |
|---|---|---|---|---|---|
| | | T = 1 M | T = 2 M | T = 3 M | T = 4 M |
| Initial pH 4.23 | Controlled Room Temp. | No | No | No | No |
| | 30° | No | No | No | No |
| | 40° | No | No | No | No |
| pH 4.58 | Controlled Room Temp. | No | No | No | No |
| | 30° | No | No | No | No |
| | 40° | No | No | No | No |
| pH 4.86 | Controlled Room Temp. | No | No | No | No |
| | 30° | No | No | No | No |
| | 40° | No | No | No | No |
| pH 5.32 | Controlled Room Temp. | No | No | No | No |
| | 30° | No | No | No | No |
| | 40° | No | No | No | No |

TABLE 15

(Data for Formulation G, Months 5-9)

| pH of Formulation | Storage Condition | Crystal Observed (Yes/No) | | | | |
|---|---|---|---|---|---|---|
| | | T = 5 M | T = 6 M | T = 7 M | T = 8 M | T = 9 M |
| Initial pH 4.23 | Controlled Room Temp. | No | No | No | No | No |
| | 30° | No | No | No | No | No |
| | 40° | No | No | No | No | No |
| pH 4.58 | Controlled Room Temp. | No | No | No | No | No |
| | 30° | No | No | No | No | No |
| | 40° | No | No | No | No | No |
| pH 4.86 | Controlled Room Temp. | No | No | No | No | No |
| | 30° | No | No | No | No | No |
| | 40° | No | No | No | No | No |
| pH 5.32 | Controlled Room Temp. | No | No | No | No | Yes |
| | 30° | No | Yes | Yes | Yes | Yes |
| | 40° | No | Yes | Yes | Yes | Yes |

TABLE 16

(Data for Formulation H, Months 1-4)

| pH of Formulation | Storage Condition | Crystal Observed (Yes/No) | | | |
|---|---|---|---|---|---|
| | | T = 1 M | T = 2 M | T = 3 M | T = 4 M |
| Initial pH 4.02 | Controlled Room Temp. | No | No | No | No |
| | 30° | No | No | No | No |
| | 40° | No | No | No | No |
| pH 4.21 | Controlled Room Temp. | No | No | No | No |
| | 30° | No | No | No | No |
| | 40° | No | No | No | No |
| pH 4.54 | Controlled Room Temp. | No | No | No | No |
| | 30° | No | Yes | Yes | Yes |
| | 40° | No | No | No | No |
| pH 4.84 | Controlled Room Temp. | No | No | No | No |
| | 30° | No | No | No | No |
| | 40° | No | No | No | Yes |
| pH 5.35 | Controlled Room Temp. | No | Yes | Yes | Yes |
| | 30° | No | Yes | Yes | Yes |
| | 40° | Yes | Yes | Yes | Yes |

TABLE 17

(Data for Formulation H, Months 5-9)

| pH of Formulation | Storage Condition | Crystal Observed (Yes/No) | | | | |
|---|---|---|---|---|---|---|
| | | T = 5 M | T = 6 M | T = 7 M | T = 8 M | T = 9 M |
| Initial pH 4.02 | Controlled Room Temp. | No | No | No | No | No |
| | 30° | No | No | No | No | No |
| | 40° | No | No | No | No | No |
| pH 4.21 | Controlled Room Temp. | No | No | No | No | No |
| | 30° | No | No | No | No | No |
| | 40° | No | No | No | No | No |
| pH 4.54 | Controlled Room Temp. | No | No | No | Yes | Yes |
| | 30° | Yes | Yes | Yes | Yes | Yes |
| | 40° | No | No | No | No | No |

TABLE 17-continued (Data for Formulation H, Months 5-9)

| | | Crystal Observed (Yes/No) | | | | |
|---|---|---|---|---|---|---|
| pH of Formulation | Storage Condition | T = 5 M | T = 6 M | T = 7 M | T = 8 M | T = 9 M |
| pH 4.84 | Controlled Room Temp. | Yes | No | No | No | No |
| | 30° | Yes | No | No | No | No |
| | 40° | Yes | No | No | No | No |
| pH 5.35 | Controlled Room Temp. | Yes | Yes | Yes | Yes | Yes |
| | 30° | Yes | Yes | Yes | Yes | Yes |
| | 40° | Yes | Yes | Yes | Yes | Yes |

As illustrated in Tables 8-17, formulations with Sepineo appear to be less stable than formulations without Sepineo regardless of the pH of the formulation.

Example 4

The solubility of SHR0302 was determined in water at varying pH values in a phosphate buffer. FIG. 1 illustrates a plot of SHR0302 (also known as ARQ-250) concentration in μg/mL in water as a function of pH in a phosphate buffer system. FIG. 1 illustrates that SHR0302 solubility in water decreases as pH levels increase. FIG. 1 further suggests that SHR0302 remains in solution in the lower pH samples, while the higher pH samples could have SHR0302 solubility challenges.

Example 5

Figure 2:
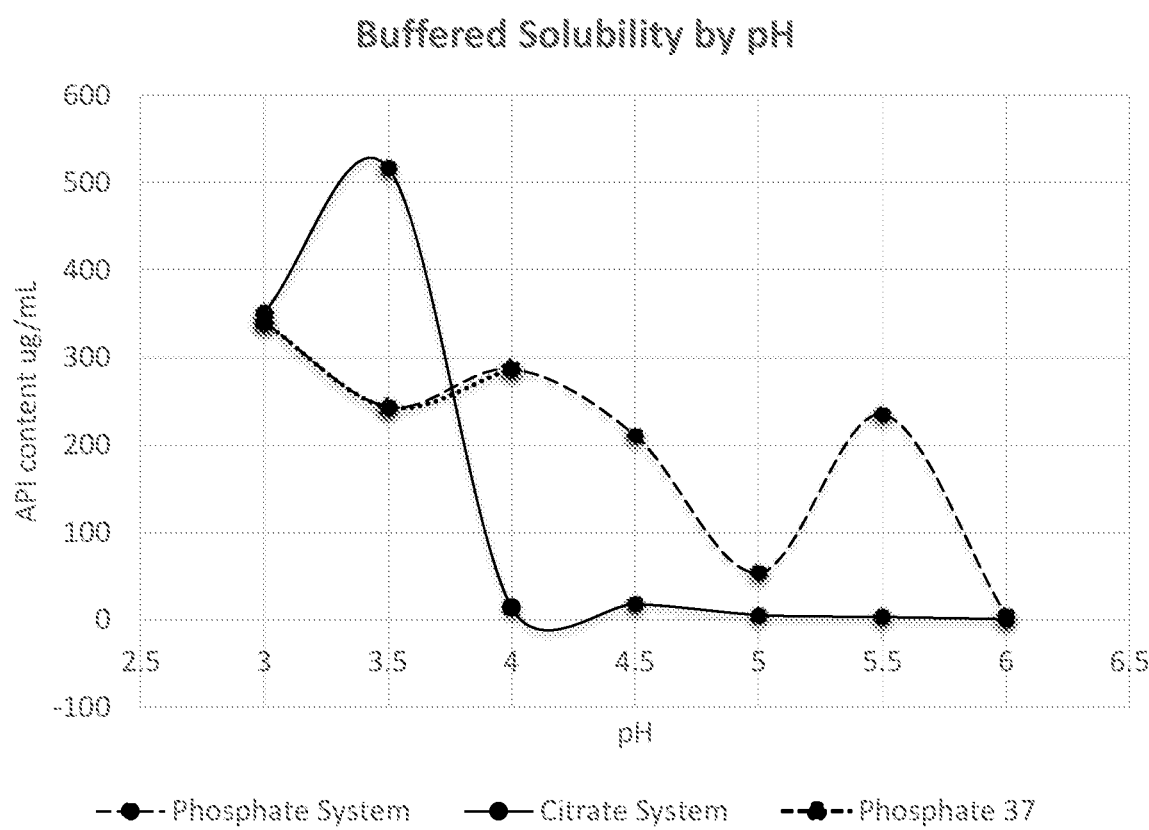
FIG. 2 illustrates a plot of SHR0302 (also known as ARQ-250) concentration in μg/mL in water as a function of pH in phosphate and citrate buffer systems. The results illustrate that SHR0302 solubility in water decreases as pH levels increase.

The solubility of SHR0302 was determined in water at varying pH values in various buffer systems. FIG. 2 illustrates a plot of SHR0302 concentration in μg/mL in water as a function of pH in two phosphate buffer systems and a citrate buffer system. FIG. 2 illustrates that SHR0302 solubility in water decreases as pH levels increase. FIG. 2 further suggests that SHR0302 remains in solution in the lower pH samples, while the higher pH samples could have SHR0302 solubility challenges.

Example 6

The pharmaceutical compositions set forth in Table 18 were prepared:

TABLE 18

| Ingredient | Formulation #1 (% w/w) | Formulation #2 (% w/w) |
|---|---|---|
| SHR0302 | 0.5 | 0.5 |
| DMSO | 35.0 | 35.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Purified Water | Q.S to 100 | Q.S to 100 |
| 25% Trolamine | pH to 4.5-5.0 | pH to 4.5-5.0 |
| 10% (w/v) HCl | pH to 4.5-5.0 | pH to 4.5-5.0 |

Example 7

IVPT results comparing prototype SHR0302 formulations with and without laureth-4 used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 3:
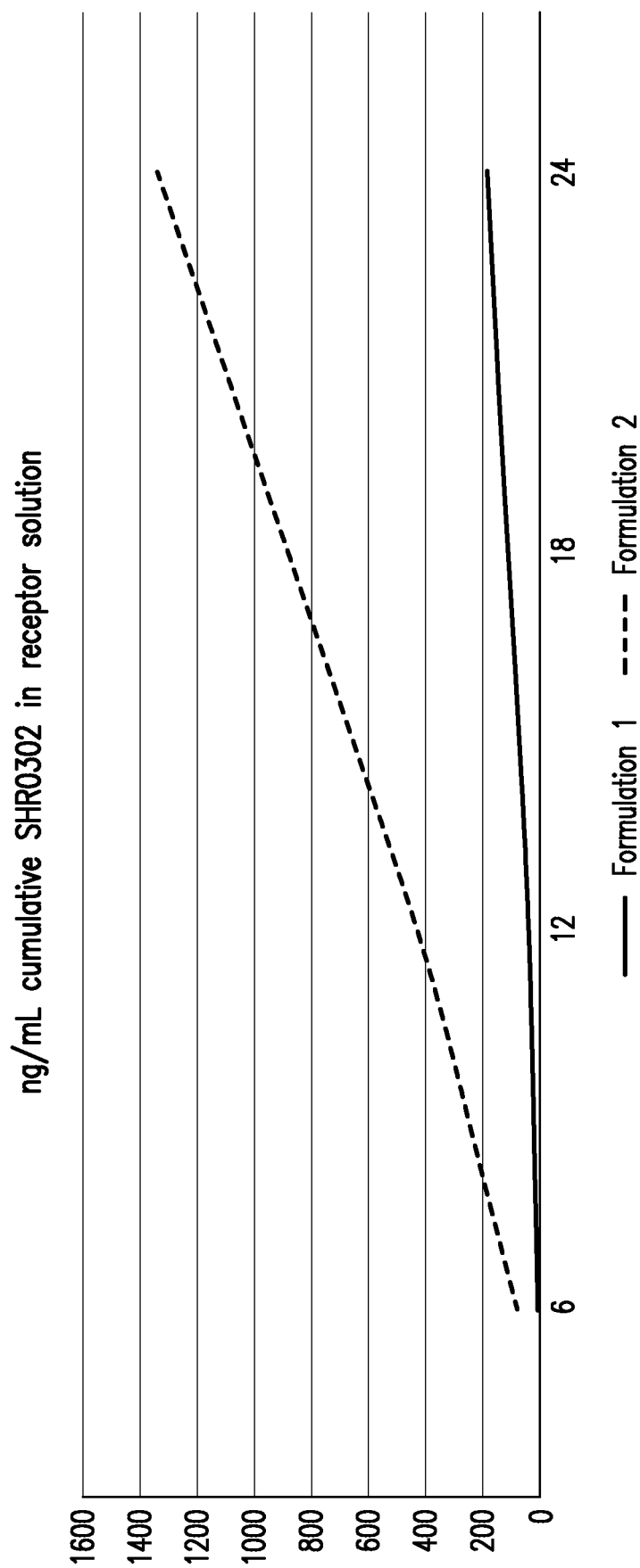
FIG. 3 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302 and DMSO.
Figure 4:
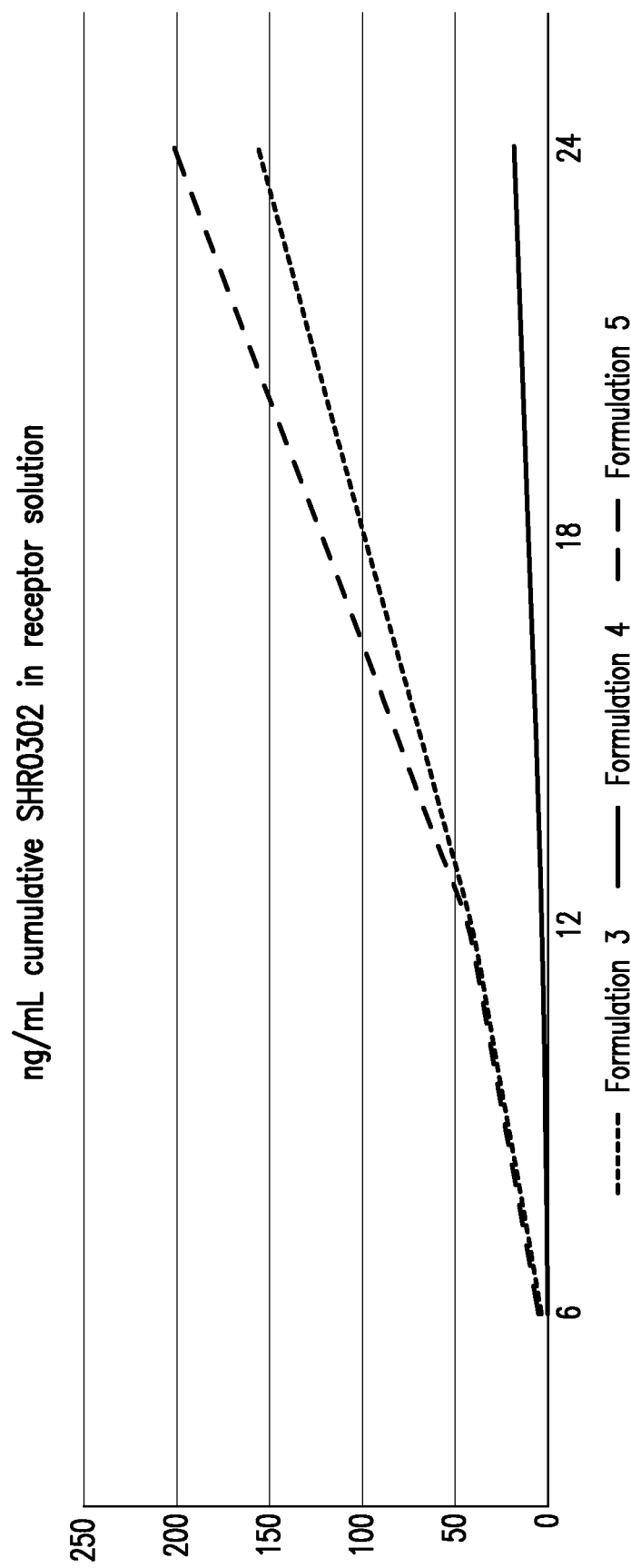
FIG. 4 illustrates IVPT results comparing three exemplary SHR0302 formulations comprising varying concentrations of xanthan gum and laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302 and NMP.

The results of this experiment (reported as ng/mL cumulative SHR0302 in receptor solution) are shown in Table 19 and depicted in FIG. 3. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the topical formulations. The Formulation #1 and #2 from Example 4 that were formulated for the IVPT study were formulated at a pH of 5.5-5.9.

TABLE 19

| Formulation # | 1 hr | 3 hr | 6 hr | 12 hr | 24 hr | Epidermis 24 hr | Dermis 24 hr |
|---|---|---|---|---|---|---|---|
| 1 | 0.0 | 0.3 | 4.7 | 36.5 | 182.5 | 71.3 | 125.6 |
| 2 | 0.0 | 8.1 | 79.4 | 423.3 | 1340.6 | 52.9 | 435.5 |

Example 8

The pharmaceutical compositions set forth in Table 20 were prepared:

TABLE 20

| Ingredient | Formulation #3 (% w/w) | Formulation #4 (% w/w) | Formulation #5 (% w/w) |
|---|---|---|---|
| SHR0302 | 0.3 | 0.3 | 0.3 |
| N-Methyl-2 Pyrrolidone | 20.0 | 20.0 | 20.0 |
| Laureth-4 | 4.0 | 0.1 | 4.0 |
| Butylated Hydroxytoluene | 0.05 | 0.05 | 0.05 |
| Methylparaben | 0.2 | 0.2 | 0.2 |
| Propylparaben | 0.05 | 0.05 | 0.05 |
| Crodafos CES | 10.0 | 10.0 | 10.0 |
| Isopropyl Palmitate | 5.0 | 5.0 | 5.0 |
| White Petrolatum (Protopet 1 S) | 5.0 | 5.0 | 5.0 |
| Propylene Glycol | 15.0 | 15.0 | 15.0 |
| PEG 200 | 15.0 | 15.0 | 15.0 |
| 1N Sodium Hydroxide | 3.5 | 3.5 | 3.5 |
| Xanthan Gum | — | 0.2 | 0.2 |
| Purified Water | Q.S to 100 | Q.S to 100 | Q.S to 100 |
| 10% Sodium Hydroxide | pH to 4.5-5.0 | pH to 4.5-5.0 | pH to 4.5-5.0 |

Example 9

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% BSA in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 5:
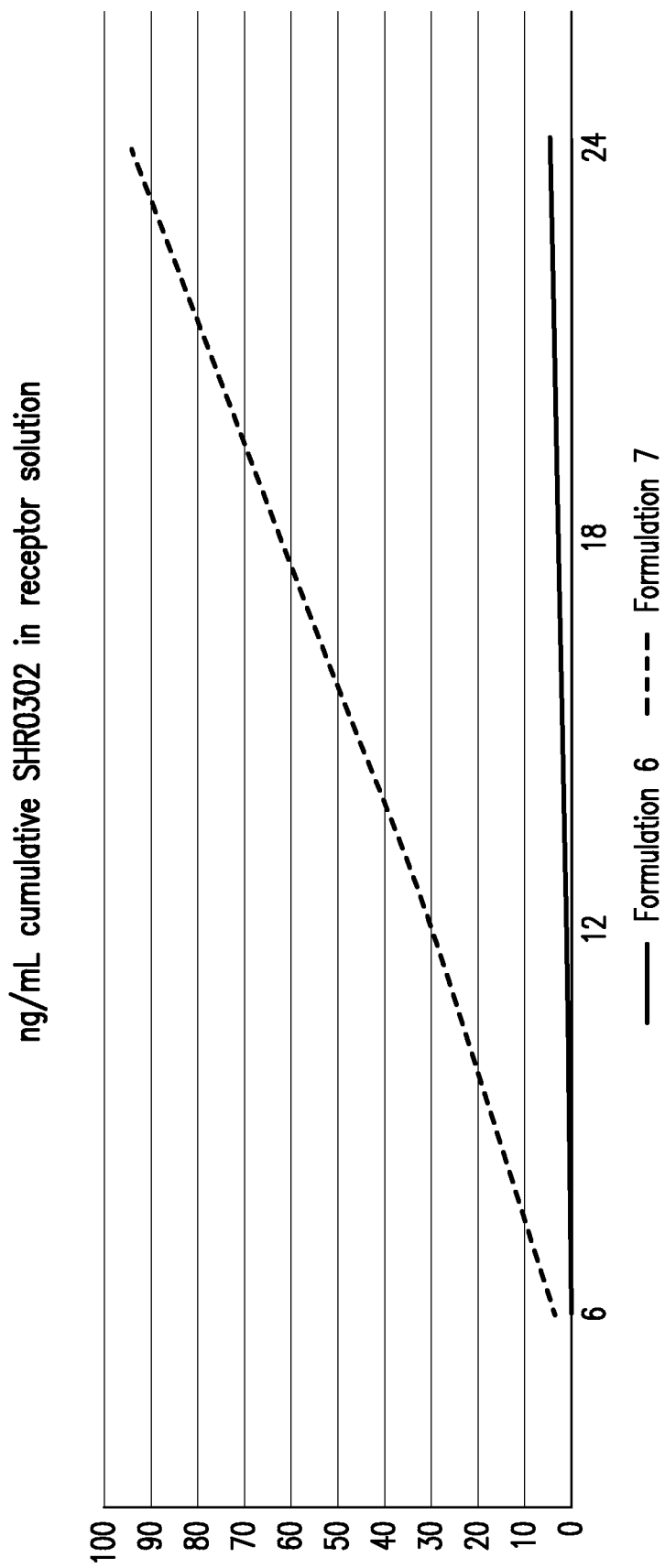
FIG. 5 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 21 and depicted in FIG. 5. The addition of laureth-4 to the topical formulation containing NMP showed a surprising and striking increase in skin penetration when compared to a nearly identical formulation with minimal amounts laureth-4. These results demonstrate the efficacy of laureth-4 as a skin penetration enhancer in the topical formulations. The Formulation #3, #4, and #5 from Example 6 that were formulated for the IVPT study were formulated at a pH of 5.5-5.9.

TABLE 21

| Example # | 1 hr | 3 hr | 6 hr | 12 hr | 24 hr | Epidermis 24 hr | Dermis 24 hr |
|---|---|---|---|---|---|---|---|
| 3 | 0 | 0.5 | 3.5 | 41.1 | 156.4 | 15 | 63 |
| 4 | 0 | 0 | 0.1 | 2.7 | 18.4 | 33.1 | 15.0 |
| 5 | 0 | 0.6 | 4.8 | 42.8 | 201.2 | 25.9 | 62.3 |

Example 10

The pharmaceutical compositions set forth in Table 22 of the following compositions were prepared:

TABLE 22

| Ingredients | Formulation #6 (% w/w) | Formulation #7 (% w/w) |
|---|---|---|
| SHR0302 | 0.5 | 0.5 |
| Sodium Phosphate Monobasic, Anhydrous | 0.5 | 0.5 |
| Methylparaben | 0.1 | 0.1 |
| Propylparaben | 0.02 | 0.02 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Polysorbate 60 | 10.0 | 10.0 |
| Hydroxyethyl Cellulose | 0.5 | 0.5 |
| Laureth 4 | — | 4.0 |
| Crodafos CES | 10.0 | 10.0 |
| White Petrolatum | 10.0 | 10.0 |
| Dimethicone, 350 cst | 1.0 | 1.0 |
| Purified Water | Q.S. to 100 | Q.S. to 100 |

Example 11

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

The results of this experiment (reported as ng/mL cumulative SHR0302 in receptor solution) are shown in Table 23 and depicted in FIG. 5. The addition of laureth-4 to the topical formulation containing a 1:1:1 ratio of DMSO:DMI:DEGEE showed a surprising and striking increase in skin penetration when compared to a nearly identical formulation without laureth-4. These results demonstrate the efficacy of laureth-4 as a skin penetration enhancer in the topical formulations.

TABLE 23

| Example # | 1 hr | 3 hr | 6 hr | 12 hr | 24 hr | Epidermis 24 hr | Dermis 24 hr |
|---|---|---|---|---|---|---|---|
| 6 | 0.0 | 0.0 | 0.0 | 1.1 | 4.6 | 22.8 | 10.0 |
| 7 | 0.0 | 0.0 | 3.5 | 62.6 | 95.0 | 155.2 | 115.1 |

Example 12

The pharmaceutical compositions set forth in Table 24 were prepared:

TABLE 24

| Ingredients | Formulation #8 (% w/w) | Formulation #9 (% w/w) |
|---|---|---|
| SHR0302 | 0.5 | 0.5 |
| Sodium Phosphate Monobasic, Anhydrous | 0.5 | 0.5 |
| Glycerin | 5.0 | 5.0 |
| Methylparaben | 0.1 | 0.1 |
| Propylparaben | 0.02 | 0.02 |
| Butylated hydroxytoluene | 0.05 | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Xanthan Gum | 0.2 | 0.2 |
| Laureth 4 | — | 4.0 |
| Polyethylene (2) stearyl ether | 5.0 | 5.0 |
| Polyethylene (21) stearyl ether | 5.0 | 5.0 |
| Cetostearyl Alcohol | 6.0 | 6.0 |
| PPG 15 Stearyl Ether | 5.0 | 5.0 |
| Purified Water | Q.S to 100 | Q.S to 100 |

Example 13

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 6:
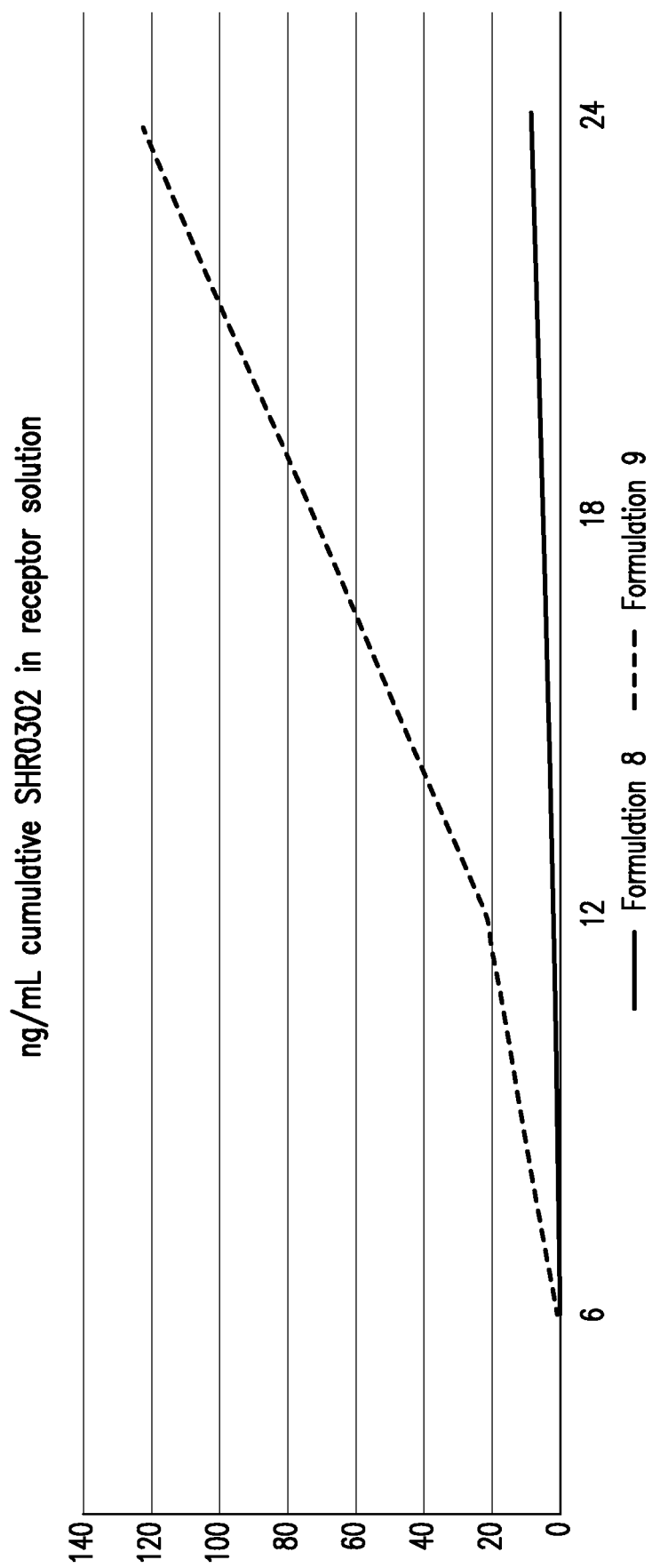
FIG. 6 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 25 and depicted in FIG. 6. The addition of laureth-4 to the topical formulation containing a 1:1:1 ratio of DMSO:DMI:

DEGEE showed a surprising and striking increase in skin penetration when compared to a nearly identical formulation without laureth-4. These results demonstrate the efficacy of laureth-4 as a skin penetration enhancer in the topical formulations.

TABLE 25

| Example # | 1 hr | 3 hr | 6 hr | 12 hr | 24 hr | Epidermis 24 hr | Dermis 24 hr |
|---|---|---|---|---|---|---|---|
| 8 | 0.0 | 0.0 | 0.0 | 1.8 | 8.3 | 41.5 | 27.2 |
| 9 | 0.0 | 0.0 | 1.1 | 21.9 | 124.3 | 191.4 | 119.6 |

Example 14

The pharmaceutical compositions set forth in Table 26 was prepared:

TABLE 26

| Ingredients | Formulation #10 (% w/w) | Formulation #11 (% w/w) |
|---|---|---|
| SHR0302 | 0.5 | 0.5 |
| DMSO | 30.0 | 30.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Edetate Disodium, Dihydrate | 0.05 | 0.05 |
| D-Limonene | 0.1 | 0.1 |
| Purified Water | Q.S to 100 | Q.S to 100 |
| 25% Trolamine | pH to 4.5-5.0 | pH to 4.5-5.0 |
| 10% (w/v) HCl | pH to 4.5-5.0 | pH to 4.5-5.0 |

Example 15

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 7:
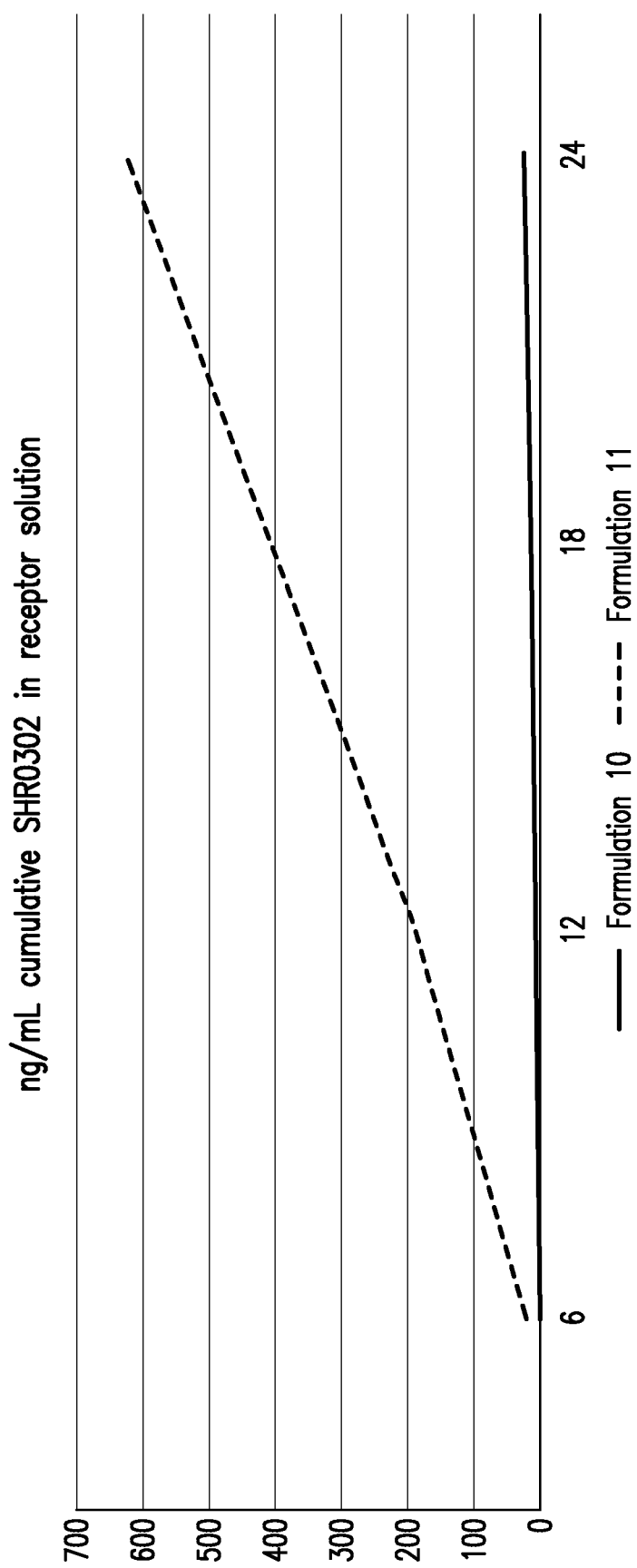
FIG. 7 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.
Figure 8:
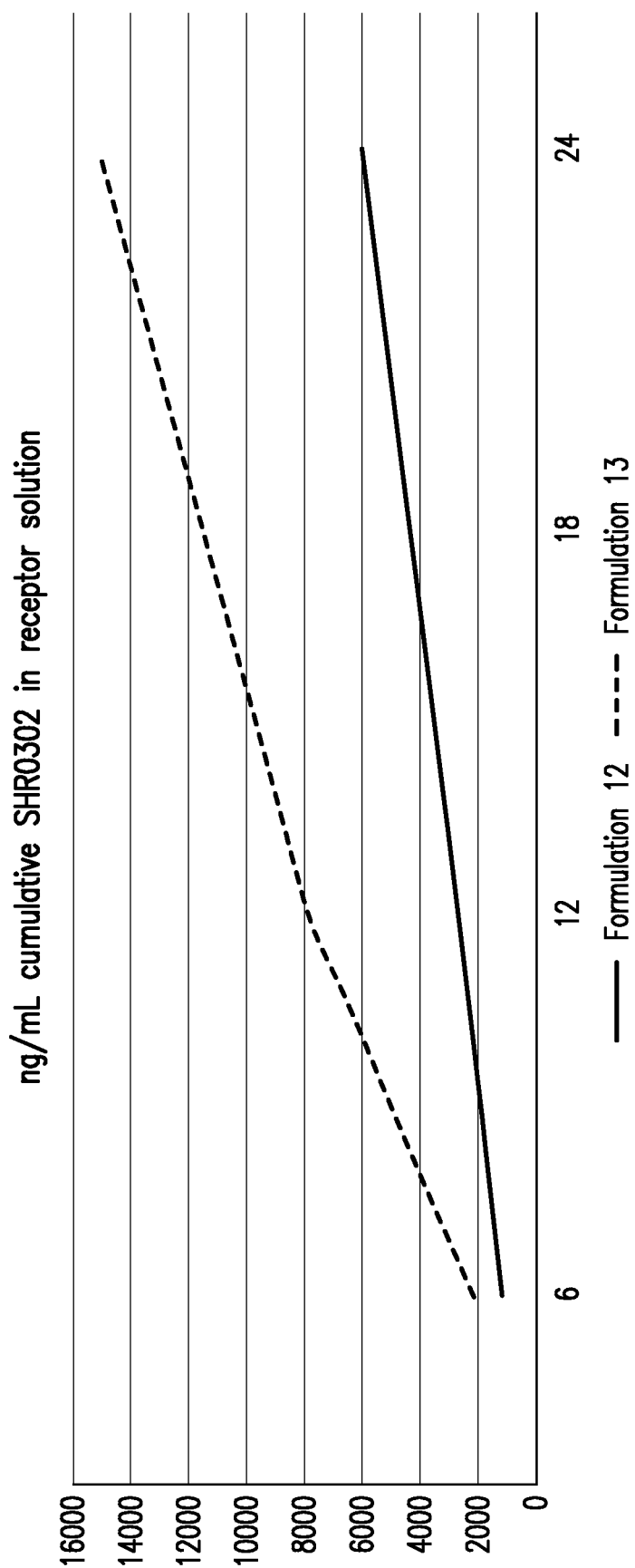
FIG. 8 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 27 and depicted in FIG. 7. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the topical formulations.

TABLE 27

| Formulation # | 1 hr | 3 hr | 6 hr | 12 hr | 24 hr | Epidermis 24 hr | Dermis 24 hr |
|---|---|---|---|---|---|---|---|
| 10 | 0.0 | 0.0 | 0.0 | 4.2 | 23.6 | 495.5 | 98.6 |
| 11 | 0.0 | 1.8 | 20.7 | 187.6 | 625.3 | 191.8 | 226.8 |

Example 16

The pharmaceutical compositions set forth in Table 28 were prepared:

TABLE 28

| Ingredients | Formulation #12 (% w/w) | Formulation #13 (% w/w) |
|---|---|---|
| SHR0302 | 0.5 | 0.5 |
| Sodium Phosphate Monobasic, Anhydrous | 0.5 | 0.5 |
| Glycerin | — | 5.0 |
| Methylparaben | 0.1 | 0.1 |
| Propylparaben | 0.02 | 0.02 |
| Butylated hydroxytoluene | — | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Polysorbate 60 | 10.0 | — |
| Xanthan Gum | — | 0.2 |
| Hydroxyethyl Cellulose | 0.5 | — |
| Laureth 4 | 4.0 | 4.0 |
| Crodafos CES | 10.0 | — |
| Polyethylene (2) stearyl ether | — | 5.0 |
| Polyethylene (21) stearyl ether | — | 5.0 |
| Cetostearyl Alcohol | — | 6.0 |
| White Petrolatum | 10.0 | — |
| PPG 15 Stearyl Ether | — | 5.0 |
| Dimethicone, 350 cst | 1.0 | — |
| Purified Water | Q.S. to 100 | Q.S to 100 |

Formulation #12 was prepared as follows: 38.93 grams of purified water was charged to the main manufacturing vessel. 0.50 grams of sodium phosphate monobasic, anhydrous was added to the water in the main manufacturing vessel and mixed until a clear solution was obtained. In a separate container labeled "Part B" 10.04 grams dimethyl sulfoxide, 10.16 grams of diethylene glycol monoethyl ether (Transcutol P®) and 10.14 grams dimethyl isosorbide were blended together. Two preservatives (0.10 grams of methylparaben and 0.021 grams of propylparaben) and 0.62 grams of the JAK inhibitor SHR0302 were added to "Part B" and stirred until completely dissolved. The entire contents of the container labeled "Part B" was added to the main manufacturing vessel and mixed until a clear solution was obtained. Polysorbate 60 was added (10.15 grams) to the main manufacturing vessel and mixed to form a hazy viscous liquid. Hydroxypropyl cellulose (0.51 grams) was added to the main manufacturing vessel and mixed to form a hazy viscous liquid. In a separate container labeled "Part E" 10.15 white petrolatum, 10.16 grams Crodafos™ CES, and 4.0 grams laureth-4 were combined and heated to 66° C. The main manufacturing vessel was heated to 68° C. Using a homogenizer (25 mm head set at 10,230 rpm) the entire contents of "Part E" were added to the main manufacturing vessel and homogenized for 5 minutes. Dimethicone (1.01 grams) was added to the main manufacturing vessel and homogenized for 2 additional minutes. Purified water (0.76 grams) was added to Q.S. ad the batch to 100%.

Formulation #13 was prepared as follows: 38.63 grams of purified water was charged to the main manufacturing vessel. Glycerin (5.1 grams) and 0.50 grams of sodium phosphate monobasic, anhydrous was added to the water in the main manufacturing vessel and mixed until a clear solution was obtained. Xanthan gum (0.2 grams) was added to the main manufacturing vessel and mixed for 59 minutes. In a separate container labeled "Part D" 10.08 grams dimethyl sulfoxide, 10.10 grams of diethylene glycol monoethyl ether (Transcutol P®), 10.06 grams dimethyl isosorbide 0.10 grams methylparaben, 0.020 grams propylparaben, 0.052 grams butylated hydroxytoluene and 0.62 grams of the JAK inhibitor SHR0302 were combined and mixed until forming a clear solution. In a third separate container labeled "Part C" 5.15 grams Polyethylene (2) stearyl ether, 5.06 grams Polyethylene (21) stearyl ether, 5.06 grams PPG 15 stearyl ether, 6.10 grams cetostearyl alcohol and 4.06 grams laureth-4 were combined and heated to 72° C. The main manufacturing vessel was heated to 74° C. Using a homogenizer (25 mm head set at 9800 rpm) the entire contents of "Part C" were added to the main manufacturing vessel and homogenized for 3 minutes. With continuous homogenization, the entire contents of "Part D" were slowly added to the main manufacturing vessel. Total homogenization time was 5 minutes. Additional purified water for this specific batch was not used to Q.S. ad the batch to 100%.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A topical pharmaceutical composition comprising a pharmaceutically effective amount of SHR0302, wherein the pharmaceutical composition has a pH of less than 4.6.

2. The topical pharmaceutical composition of claim 1, wherein the pharmaceutical composition has a pH greater than 3.8 and less than 4.6.

3. The topical pharmaceutical composition of claim 1, wherein the pharmaceutical composition has a pH between about 3.8 and about 4.2.

4. The topical pharmaceutical composition of claim 1 comprising SHR0302 in an amount of about 0.1% w/w to about 1.0% w/w.

5. The topical pharmaceutical composition of claim 1, further comprising laureth-4.

6. The topical pharmaceutical composition of claim 5, wherein the laureth-4 is present in an amount of about 0.5% w/w to about 5% w/w.

7. The topical pharmaceutical composition of claim 1, wherein the pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment.

8. The topical pharmaceutical composition of claim 1, wherein the pharmaceutical composition inhibits crystal growth at controlled room temperature for 8 months.

9. A topical pharmaceutical composition comprising a pharmaceutically effective amount of SHR0302 and about 25% w/w of dimethyl sulfoxide.

10. The topical pharmaceutical composition of claim 9 comprising SHR0302 in an amount of about 0.1% w/w to about 1.0% w/w.

11. The topical pharmaceutical composition of claim 9 further comprising laureth-4.

12. The topical pharmaceutical composition of claim 11, wherein the laureth-4 is present in an amount of about 0.5% w/w to about 5% w/w.

13. The topical pharmaceutical composition of claim 9, wherein the pharmaceutical composition is selected from the group consisting of a cream, a lotion, an oil-in-water emulsion, a water-in-oil emulsion, a microemulsion, a nanoemulsion, a foam, a spray, a gel, a hydrophilic ointment, or a hydrophobic ointment.

14. A topical pharmaceutical composition comprising a pharmaceutically effective amount of SHR0302 and about 20% w/w to about 30% w/w of dimethyl sulfoxide, wherein the pharmaceutical composition inhibits crystal growth at controlled room temperature for 6 months.

* * * * *